United States Patent
Oh et al.

(10) Patent No.: US 6,949,654 B2
(45) Date of Patent: Sep. 27, 2005

(54) N-ALKYL-N-PHENYLHYDROXYLAMINE COMPOUNDS CONTAINING METAL CHELATING GROUPS, THEIR PREPARATION AND THEIR THERAPEUTIC USES

(75) Inventors: Eu-Gene Oh, Taejon (KR); Sung-Bo Ko, Taejon (KR); Won-Yeob Kim, Taejon (KR); Kyung-Hwa Kim, Taejon (KR); Dennis W. Choi, St. Louis, MO (US); Laura L. Dugan, St. Louis, MO (US); Tae-Cheon Kang, Chuncheon (KR); Jae-Young Koh, Seoul (KR); Kyung-Mi Kim, Sungnam (KR); In-Jae Shin, Koyang (KR)

(73) Assignee: Sam-Sung Electronics Co., Ltd., Kyunggi-do (KR)

( * ) Notice: Subject to any disclaimer, the term of this patent is extended or adjusted under 35 U.S.C. 154(b) by 70 days.

(21) Appl. No.: 10/456,024

(22) Filed: Jun. 5, 2003

(65) Prior Publication Data

US 2003/0225087 A1 Dec. 4, 2003

Related U.S. Application Data

(63) Continuation of application No. PCT/KR01/01274, filed on Jul. 26, 2001.

(51) Int. Cl.$^7$ .................. C07D 277/44; C07D 213/75; C07D 215/38; A61K 31/425; A61K 31/44
(52) U.S. Cl. ............... 546/171; 546/309; 548/195; 514/311; 514/352; 514/371
(58) Field of Search ................. 514/311, 352, 514/371; 546/171, 309; 548/195

(56) References Cited

U.S. PATENT DOCUMENTS

| 5,008,394 A | 4/1991 | Günther et al. |
| 5,827,880 A | 10/1998 | Malfroy-Camine et al. |

FOREIGN PATENT DOCUMENTS

JP    WO98/08831    3/1998

OTHER PUBLICATIONS

Database CAPLUS on STN, Acc. No. 1970:466455, GB 1195491 (Jun. 17, 1970) (abstact).*
Parnetti, L. et al., Cognitive Enhancement Therapy for Alzheimer's Disease, Drugs, 53:752–768 (1997).
Grisar J. M. et al., 2,3–Dihydro–1–benzofuran–5–ols as Analogues of α–Tocopherol That Inhibit in Vitro and ex Vivo Lipid Autoxidation and Protect Mice against Central Nervous System Trauma, J. Med. Chem., 38:453–458(1995).
Thomas G. Back and Brian P. Dyck, A Novel Camphor–Derived Selenenamide That Acts as a Glutathione Peroxidase Mimetic, J. Am. Chem. Soc., 119:2079–2083 (1997).
Sies, et al., Ebselen as Glutathione Peroxidase Mimic and as a Scavenger of Peroxynitrite, Adv. Pharmaco., 38:229–246 (1997).
Koh, et al., The Role of Zinc in Selective Neuronal Death after Transient Global Gerebral Ischemia, Science, vol. 272, 1013–1016 (1996).
Kim, et al., Zinc–Induced Cortical Neuronal Death with Features of Apoptosis and Necrosis: Mediation by Free Radicals, Neuroscience, 89:175–182 (1999).

* cited by examiner

Primary Examiner—Brian Davis

(57) ABSTRACT

The present invention provides novel N-alkyl-N-phenylhydroxylamine derivatives containing metal chelating groups, a process for preparing the same, the use of the novel compounds as therapeutics for treating and/or preventing various medical dysfunctions and diseases arising from reactive oxygen species (ROS) and/or excess Zn ions, in particular stroke, Parkinson's disease and Alzheimer's disease. The compounds of the invention possess similar or superior LPO inhibition activity to the reference compounds of Trolox and Ebselen. While showing lower toxicity, they also effectively inhibit the cerebral neuronal cell death caused by ROS and/or zinc ion, and show neuroprotective effects against ischemic neuronal degeneration.

36 Claims, 9 Drawing Sheets

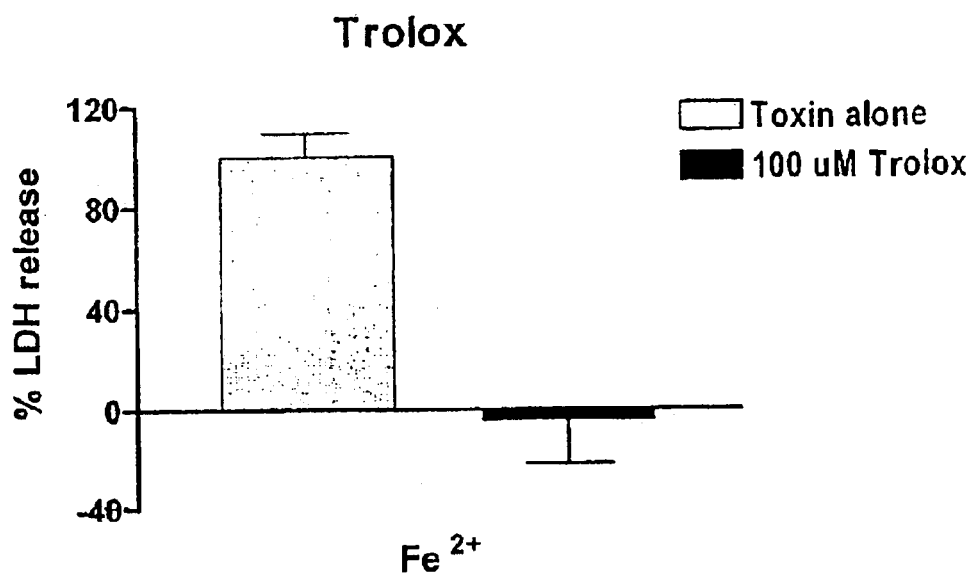
Fig. 1-a
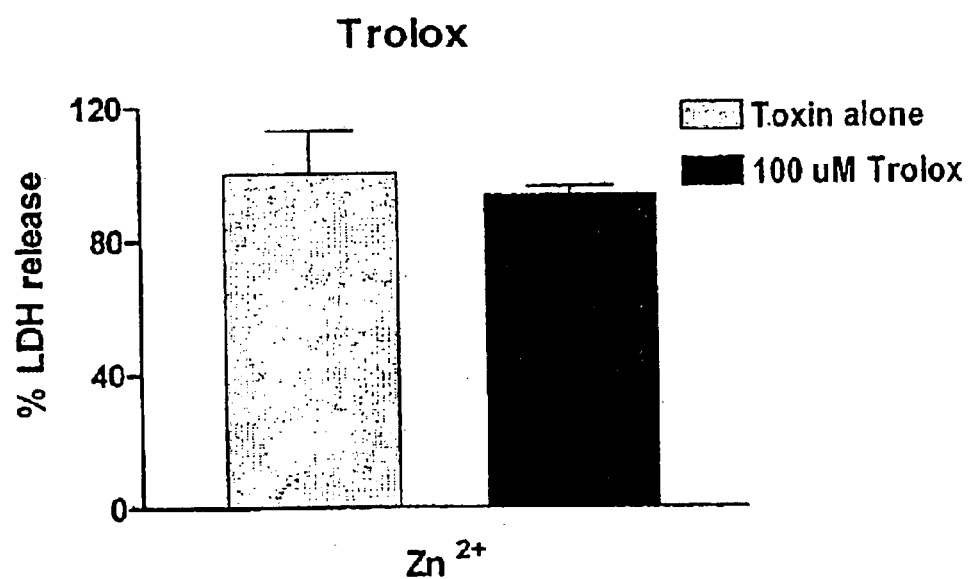
Fig. 1-b

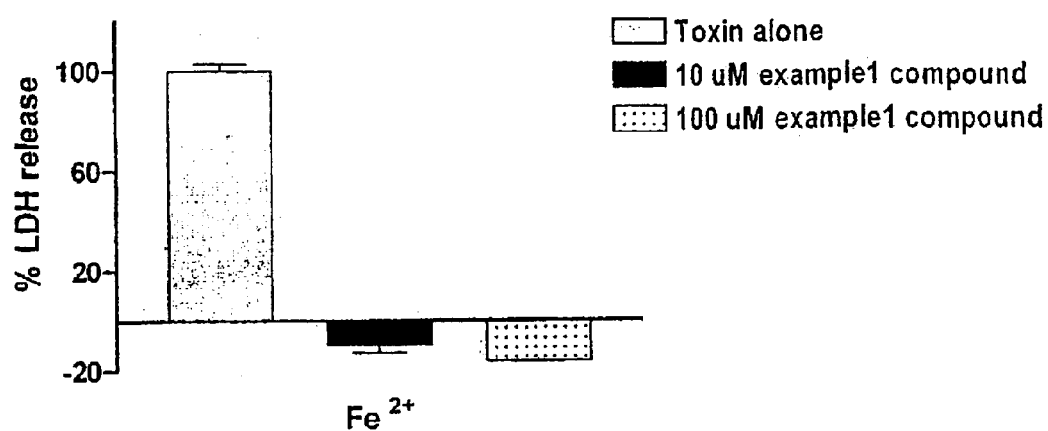
Fig. 2-a
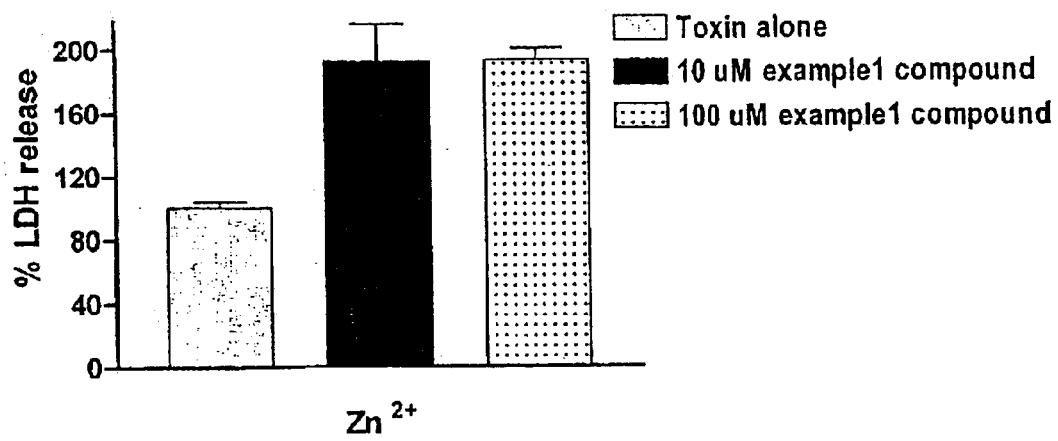
Fig. 2-b

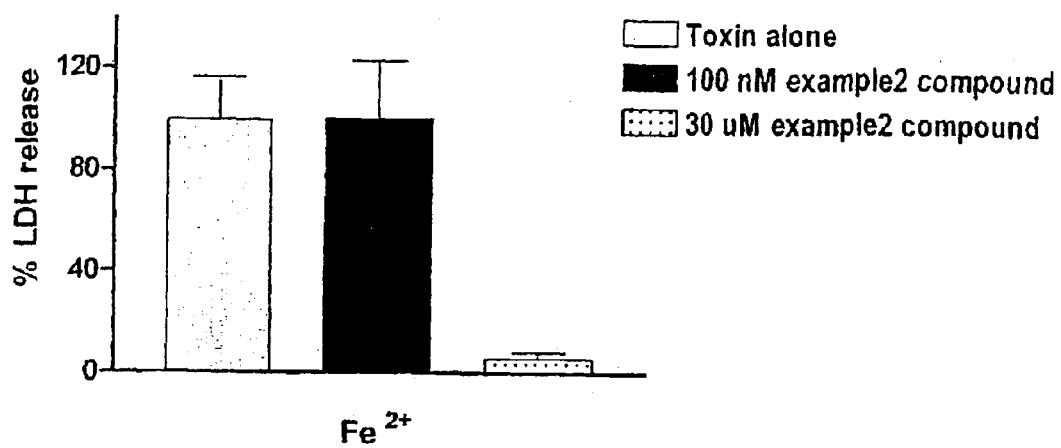
Fig. 3-a
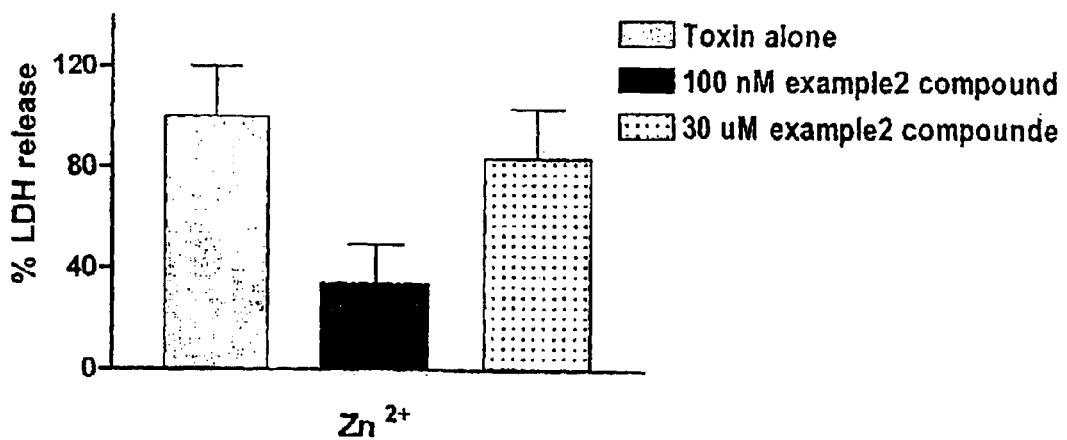
Fig. 3-b

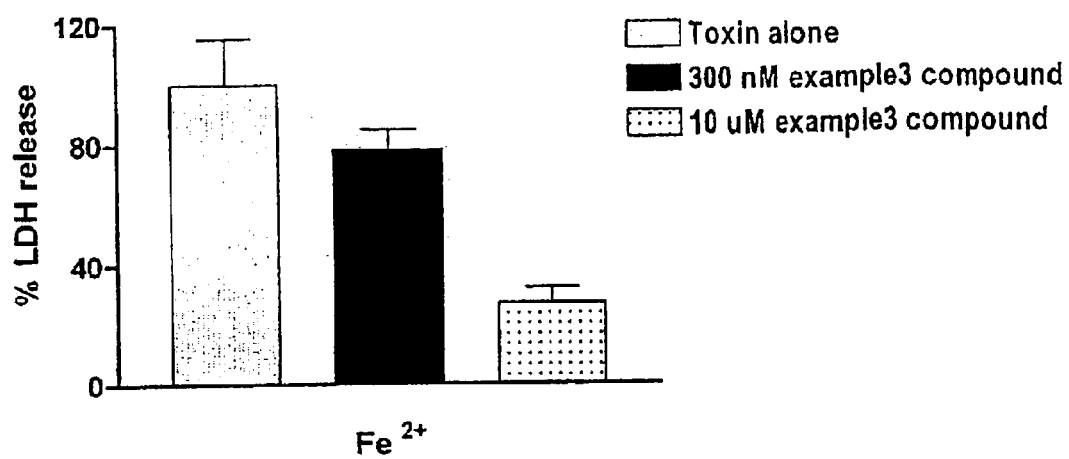
Fig. 4-a
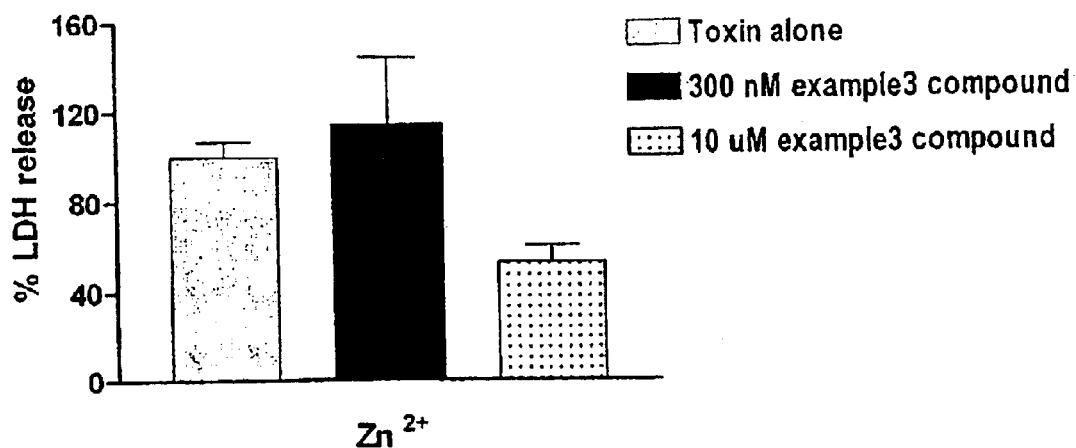
Fig. 4-b

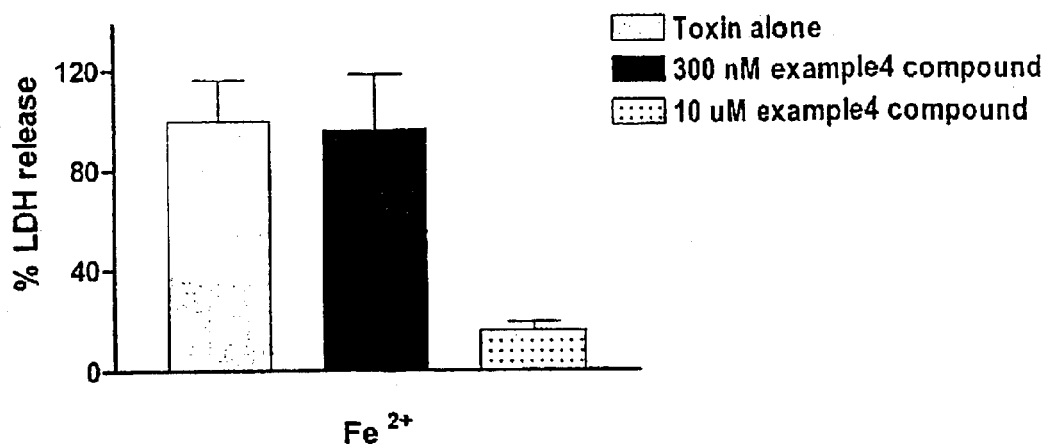
Fig. 5-a
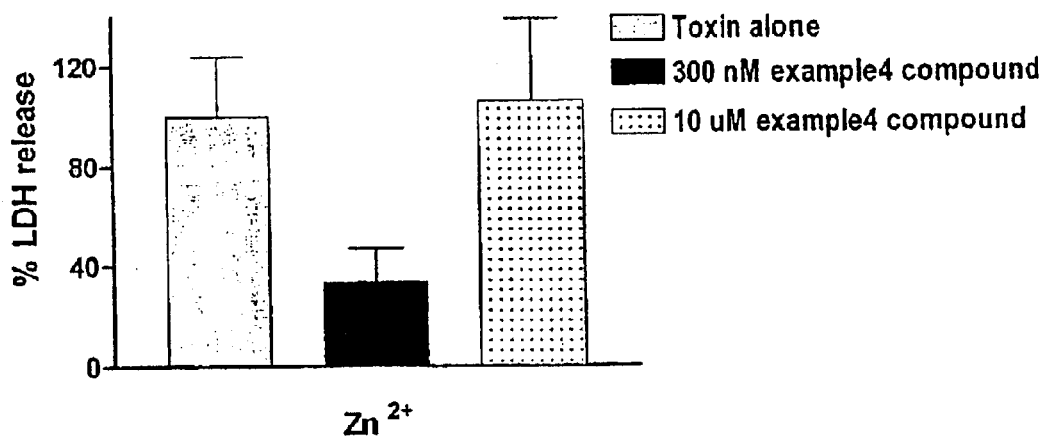
Fig. 5-b

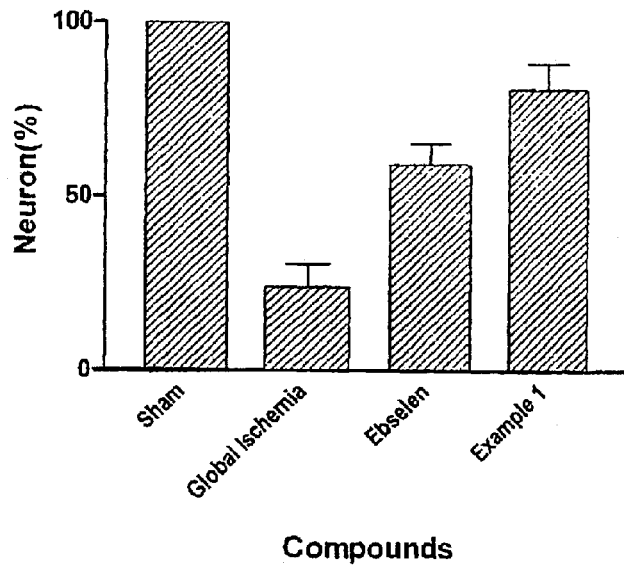
Fig. 11-a
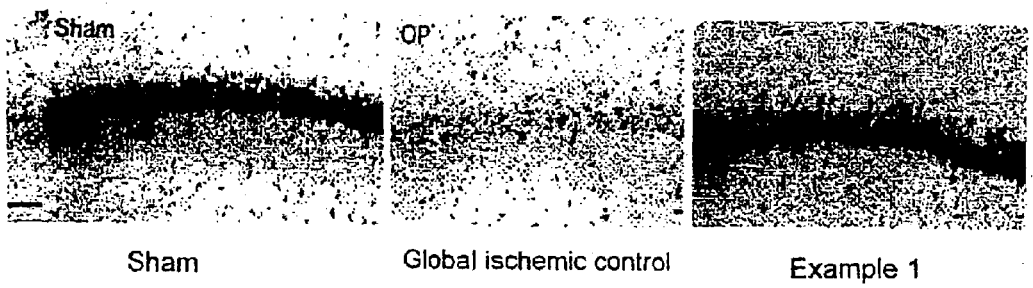
Sham　　　　　Global ischemic control　　　Example 1
Fig. 11-b

N-ALKYL-N-PHENYLHYDROXYLAMINE COMPOUNDS CONTAINING METAL CHELATING GROUPS, THEIR PREPARATION AND THEIR THERAPEUTIC USES

RELATED APPLICATIONS

This application is a continuation under 35 U.S.C. § 365 (c) claiming the benefit of the filing date of PCT Application No. PCT/KR01/01274 designating the United States, filed Jul. 26, 2001. The PCT Application was published in English as WO 03/010153 A1 on Feb. 6, 2003. The contents of the international application No. PCT/KR01/01274 and the publication WO 03/010153 A1 are incorporated herein by reference in their entirety.

BACKGROUND OF THE INVENTION

1. Field of the Invention

The present invention relates to novel N-alkyl-N-phenylhydroxylamine compounds containing metal chelating groups, their preparation and pharmaceutical compositions containing the novel compounds as active ingredients, more particularly, to novel N-alkyl-N-phenylhydroxylamine compounds containing metal chelating groups, a process for preparing the same, the use of the novel compounds as therapeutics for treating and/or preventing various medical dysfunctions and diseases caused by reactive oxygen species (ROS) and/or excess Zn ions, in particular stroke, Parkinson's disease, and Alzheimer's disease.

2. Description of the Prior Art

According to Harman's free-radical theory of ageing, successive oxidation attacks create "oxidative stress" conditions, that is, create an imbalance between the protective systems in favour of the pro-oxidants. Such attacks result in numerous molecular modifications, especially of polyunsaturated membrane lipids, proteins and nucleic acids. Human and animal organisms possess various defense mechanisms that act in synergy. Those mechanisms are of an enzymatic nature (superoxide dismutase, catalase, and glutathione peroxidase) or of a non-enzymatic nature (such as vitamins E and C, which enable physiological control of free-radical activity). With ageing, however, that protection becomes less efficient, not to say inefficient, especially as a result of the decreased activity of a large number of enzymes including those involved in such defense mechanisms. Consequently, for some disorders associated with ageing, such as atherosclerosis, cataract, non-insulin-dependent diabetes, cancer or chronic neurodegenerative disorders, numerous studies have been able to demonstrate that such conditions are associated with those "oxidative stress" conditions.

The central nervous system is especially sensitive to "oxidative stress" because of its high oxygen consumption, the relatively low levels of its antioxidant defenses and the high iron concentration of some cerebral regions. This explains why "oxidative stress" might be one of the main etiological factors of cerebral ageing, as well as of acute central nervous system disorder such as stroke, neurodegenerative disorders such as Parkinson's disease, Alzheimer's disease, and neurodegeneracies of the basal ganglia. The rate of occurrence of neurodegenerative disorders of central nervous system increases worldwide. Stroke occupies the third highest cause of death following cardiovascular diseases and malignant tumors (see: Parnetti, L. et al., Drug, 53:752 (1997)).

Antioxidants protecting neuron cells of brain from oxidative stress include vitamin E derivatives such as Trolox (see: J. Med. Chem., 38:453 (1995)), glutathione peroxidase (hereinafter, referred to as "GPx") mimics (see: Daiichi Pharmaceutical Co., Ltd., Annual Report (1999); WO 9808831; U.S. Pat. No. 5,008,394; J. Am. Chem. Soc., 119:2079–2083 (1997); Adv. Pharmacol., 38:229 (1996)), superoxide dismutase (SOD) mimics (see: U.S. Pat. No. 5,827,880), and spin trapping agents (see: J. Med. Chem., 39:4988 (1996); U.S. Pat. No. 5,475,032).

A GPx mimic is synthesized compound mimicking the function of the selenocystein from GPx active site. A well-known GPx mimic, Ebselen seems to have no major toxicity in preclinical and clinical tests and it is proposed as a potential drug for stroke. Ebselen is, however, very little soluble in water, even in the presence of an excess of glutathione (GSH), which limits its pharmacological applications.

Spin trapping agents may be developed as an antioxidant if they can trap hazardous free radicals enough, which include α-phenyl-N-tert-butylnitrone (PBN), and various derivatives of PBN have been developed. Generally, nitrone moiety increases the solubility of compounds in water. However, it has revealed shortcomings such as a low lipid peroxidation inhibition activity in vitro and a low protection of brain cells in vivo (see: Fevig, Thomas L. et al., J. Med. Chem., 39:4988–4996 (1996)).

On the other hand, zinc ion, which is present with high concentration (>10 mM) in synaptic vesicle storing brain neurotransmitters, is a necessary element in normal function of human cells. As soon as a neuron is stimulated, zinc ion is released into interstitial fluid and then plays a crucial role in signal transmission from neuron to neuron, especially signal transmission by glutamate.

Furthermore, a variety of studies have reported that zinc ion in the synapse may play a central role in the pathological phenomena of central nervous system. The exposure of brain cortex neuron cells to excess zinc results in the immediate neuron cell injury, while the concentration of zinc is similar to that of zinc released from the brain in convulsion or ischemia. Hence, zinc is supposed to evoke neuron cell injury, by way of the influx of excess zinc into neuron cells. In accordance with the above hypothesis, it was found that translocation of synapse zinc in neuron cells was a main cause of selective neuronal cell injury after transient global cerebral ischemia, rather than excitotoxicity by calcium (see: Koh, J.-Y. et al, Science, 272:1013–1016 (1996); Kim, Y.-H. et al, Neuroscience, 89: 175–182 (1999)). It is, more plausible that the neurotoxicity by the translocation of zinc may play a central role in acute neuron cell death derived from focal ischemia. Therefore, the chelation of zinc is supposed to be effective on persisting protection of neuron cells. However, the zinc chelator for the treatment and prevention of neurodegenerative disease of central nervous system is not developed yet.

SUMMARY OF THE INVENTION

The present inventors synthesized novel compounds by introducing metal chelating group into N-alkyl-N-phenylhydroxylamine, a hydrogen atom donor, and they found that the said compounds possess a protective activity in cerebral neuron cells against zinc ion, reactive oxygen species (ROS) and neuro-excitotoxic factor, while showing a low toxicity. As a result, the said compounds could be potential drug candidates for the treatment and prevention of cell death of brain cells.

The first object of the present invention is, therefore, to provide neuroprotective novel N-alkyl-N-phenylhydroxylamine compounds containing metal chelating groups.

The second object of the invention is to provide a process for preparing the said compounds.

The third object of the invention is to provide pharmaceutical compositions comprising the said compounds as an active ingredient for the treatment and prevention of medical dysfunctions and diseases such as stroke, Parkinson's disease, and Alzheimer's disease caused by reactive oxygen species and/or excess Zn ions.

The fourth object of the invention is to provide a method for treating a living body afflicted with a condition requiring an antioxidant and/or metal chelating agent, in particular acute and progressive neurodegenerative disorders, by way of administering to the living body the said pharmaceutical preparations.

BRIEF DESCRIPTION OF THE DRAWINGS

The above and the other objects, and features of the present invention will become apparent from the following descriptions given in conjunction with the accompanying drawings, in which:

FIG. 1-$a$ is a graph showing the results of combined treatment of Trolox and $Fe^{2+}$ toxin.

FIG. 1-$b$ is a graph showing the results of combined treatment of Trolox and $Zn^{2+}$ toxin.

FIG. 2-$a$ is a graph showing the results of combined treatment of compound obtained in Example 1 and $Fe^{2+}$ toxin.

FIG. 2-$b$ is a graph showing the results of combined treatment of compound obtained in Example 1 and $Zn^{2+}$ toxin.

FIG. 3-$a$ is a graph showing the results of combined treatment of compound obtained in Example 2 and $Fe^{2+}$ toxin.

FIG. 3-$b$ is a graph showing the results of combined treatment of compound obtained in Example 2 and $Zn^{2+}$ toxin.

FIG. 4-$a$ is a graph showing the results of combined treatment of compound obtained in Example 3 and $Fe^{2+}$ toxin.

FIG. 4-$b$ is a graph showing the results of combined treatment of compound obtained in Example 3 and $Zn^{2+}$ toxin.

FIG. 5-$a$ is a graph showing the results of combined treatment of compound obtained in Example 4 and $Fe^{2+}$ toxin.

FIG. 5-$b$ is a graph showing the results of combined treatment of compound obtained in Example 4 and $Zn^{2+}$ toxin.

FIG. 11-$a$ is a graph showing the protection level of cell damage in case of the treatment of the compound of the invention after ischemia.

FIG. 11-$b$ is a photomicrograph showing the protection level of cell damage in case of the treatment of the compound of the invention after ischemia.

DETAILED DESCRIPTION OF THE INVENTION

Figure 6:
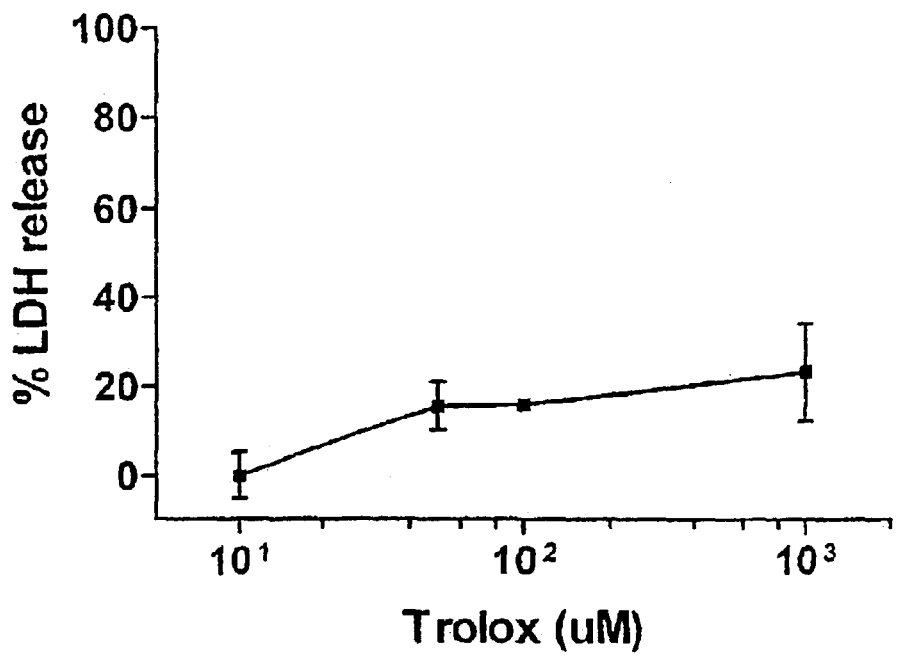
FIG. 6 is a graph showing the level of cell damage as the treatment concentration of Trolox increases.

In the first aspect, the present invention provides novel N-alkyl-N-phenylhydroxylamine derivatives containing metal chelating groups with the following general formula (I):

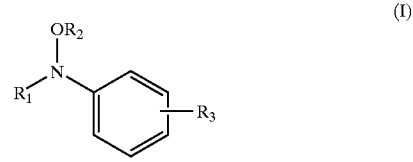

wherein, $R_1$ denotes branched alkyl, aralkyl, aryl or substituted aryl;

$R_2$ denotes hydrogen, or $COR_6$ (where, $R_6$ is alkyl or aryl); and, $R_3$ denotes metal chelating groups of $CO_2H$, $CONH_2$, or $CONR_4R_5$ (where, $R_4$ denotes hydrogen, alkyl or aryl; and, $R_5$ denotes heterocyclic unsaturated or saturated radical having 1 to 4 heteroatoms of elements nitrogen, oxygen and/or sulfur selected from the group consisting of furanyl, oxazolyl, isooxazolyl, thiophenyl, thiazolyl, isothiazolyl, pyrrolyl, imidazolyl, pyrazolyl, oxadiazolyl, thiadiazoyl, pyridyl, pyrimidinyl, pyrazinyl, pyridazinyl, triazinyl, triazolyl, tetrazolyl, it being possible for the heterocyclic radical to be substituted once or twice, identically or differently, by halogen, $C_{1-2}$-alkyl, $C_{1-4}$-alkoxy, $C_{1-4}$-alkylthio, hydroxy, mercapto, trifluoromethyl, nitro, phenyl, nitrile, carboxy or $C_{1-4}$-alkoxycarbonyl).

In this context, preferred compounds include derivatives in which $R_1$ represents branched $C_{3-8}$-alkyl, $C_{5-8}$-cycloalkyl and aryl;

$R_2$ represents hydrogen, straight or branched $C_{1-18}$ alkyl carbonyl, benzoyl, benzoyl substituted by one to three substituents, identical or different from each other, selected from the groups consisting of halogen, $C_{1-4}$-alkyl, $C_{1-4}$-alkoxy, hydroxy, trifluoromethyl, nitro, nitrile, carboxy, alkoxycarbonyl, alkoxycarbonylalkyl and methylenedioxy; and, $R_3$ represents $CO_2H$, $CONH_2$, or amides $CONR_4R_5$ (where, $R_4$ represents hydrogen, $C_{1-4}$-alkyl, aralkyl or cycloalkyl; and, $R_5$ denotes heterocyclic unsaturated or saturated radical having 1 to 4 heteroatoms of elements nitrogen, oxygen and/or sulfur from the group comprising furanyl, oxazolyl, isooxazolyl, thiophenyl, thiazolyl, isothiazolyl, pyrrolyl, imidazolyl, pyrazolyl, oxadiazolyl, thiadiazoyl, pyridyl, pyrimidinyl, pyrazinyl, pyridazinyl, triazinyl, triazolyl, tetrazolyl, it being possible for the heterocyclic radical to be substituted once or twice, identically or differently, by halogen, $C_{1-2}$-alkyl, $C_{1-4}$-alkoxy, $C_{1-4}$-alkylthio, hydroxy, mercapto, trifluoromethyl, nitro, phenyl, nitrile, carboxy and/or $C_{1-4}$-alkoxycarbonyl).

More preferred compounds include derivatives in which $R_1$ represents isopropyl, tert-butyl, cyclopentyl, cyclohexyl, phenyl;

$R_2$ represents hydrogen, acetyl, propionyl, benzoyl; and, $R_3$ represents $CO_2H$, $CONH_2$, or amides $CONR_4R_5$ (where, $R_4$ represents hydrogen, methyl, ethyl, propyl, benzyl, cyclopentyl or cyclohexyl; and, $R_5$ denotes heterocyclic unsaturated or saturated radical having 1 to 4 heteroatoms of elements nitrogen, oxygen and/or sulfur from the group comprising oxazolyl, thiazolyl, isothiazolyl, imidazolyl, pyrazolyl, thiadiazoyl, pyridyl, pyrimidinyl, pyrazinyl, pyridazinyl, triazinyl, triazolyl, tetrazolyl it being possible for the heterocyclic radical to be substituted once or twice, identically or differently, by fluorine, chlorine, bromine, methyl, methoxy, ethoxy, methylmercapto, hydroxy, mercapto, trifluoromethyl, nitro, phenyl, nitrile, carboxy, methoxycarbonyl and/or ethoxycarbonyl).

The compounds of the invention possess similar or superior LPO inhibition activity to the reference compounds of Trolox and Ebselen. While showing lower toxicity, they also effectively inhibit the cerebral neuronal cell death caused by ROS and/or zinc ion and show neuroprotective effects against ischemic neuronal degeneration.

The compounds of the invention, particularly the compound synthesized in Example 1 below, have a very low toxicity $LD_{50} \geq 7,000$ mg/kg in the case of oral administration in rats, and $\geq 750$ mg/kg in the case of intraperitoneal administration in rats. Therefore, one of the advantages of the invention is that the novel compounds can be administered at vastly higher levels than other known antioxidants, such as Ebselen ($LD_{50}$ values of Ebselen obtained in mice were $\geq 6,810$ mg/kg in the case of oral administration, and 740 mg/kg in the case of intraperitoneal administration. Similarly, the $LD_{50}$ values of Ebselen obtained in rats were $\geq 6,810$ mg/kg in the case of oral administration and 580 mg/kg in the case of intraperitoneal administration). Accordingly, large doses of the compound may be administered immediately post stroke or other trauma to significantly reduce oxidative damage.

In the second aspect, the present invention provides a process for the preparation of the compounds of formula (I) above (wherein, $R_3$ is $CONR_4R_5$), which is illustrated in the following reaction scheme:

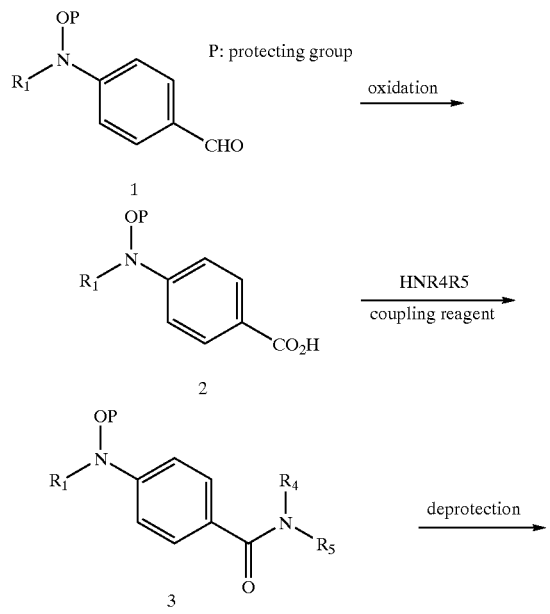

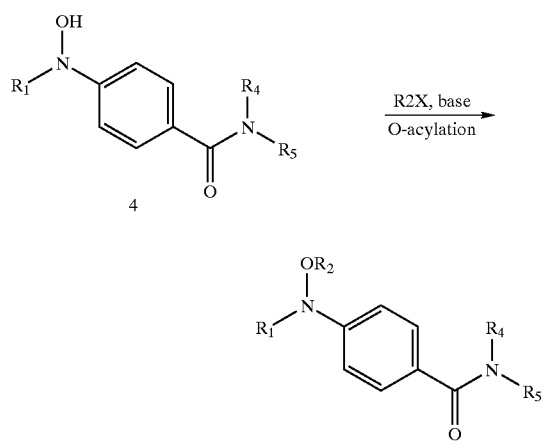

O-Protected alkylhydroxyaminobenzaldehydes 1 are oxidized to give carboxylic acids 2, which then undergo amide-coupling with $HNR_4R_5$ to provide amides 3. Removal of protecting group follows, and then N-hydroxy group of the compounds 4 is acylated to produce N-acylhydroxy group in the presence of proper base for the pharmaceutical use.

In the third aspect, the present invention provides pharmaceutical compositions comprising a pharmaceutically acceptable carrier and a pharmaceutically effective amount of a compound of formula (I) above or a pharmaceutically acceptable salts thereof. A neuroprotective agent comprising the compound of formula (I) as an active ingredient, is preferably provided.

In the fourth aspect, the present invention provides a method for treating a living body afflicted with a condition requiring an antioxidant and/or metal chelating agent, in particular acute and progressive neurodegenerative disorders, comprising a step of administering to the living body said pharmaceutical composition.

As previously mentioned, the compounds of the present invention have been found to be effective in relieving various effects resulting from ROS and/or excess Zn ions. These compounds are useful as therapeutics for treating and/or preventing a wide variety of medical dysfunctions and diseases including, but not limited to, acute central nervous system (CNS) disorders and neurodegerative conditions.

When employed as pharmaceuticals, the compounds of the invention are typically administered in the form of a pharmaceutical composition comprising at least one active compound of the invention and a pharmaceutically acceptable carrier or vehicle suitable for use in pharmaceutical compositions.

In general, the compounds of the invention are administered in a pharmaceutically effective amount. The amount of the compound actually administered will typically be determined by a physician, in light of relevant circumstances, including the condition to be treated, the chosen route of administration, the actual compound administered, the age, weight, and response of the individual patient, the severity of the patient's symptoms, and the like. The dosage used ranges from 10 mg to 500 mg in one or several administrations per day.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions.

The compositions for oral administration can take the form of bulk liquid dilutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the N-alkyl-N-phenylhydroxylamine compounds containing metal chelating groups of the invention is usually a minor component (from about 0.1 to about 50% by weight or preferably from about 1 to about 40% by weight) with the remainder being various vehicles or carriers and processing acids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the present compound in such compositions is typically a minor component, often being from about 0.05 to 10% by weight with the remainder being the injectable carrier and the like.

The components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of the invention can also be administered in sustained release forms or from sustained release drug delivery systems. A description of representative sustained release materials can be found in the incorporated materials in *Remington's Pharmaceutical Sciences*.

The following Examples are provided to illustrate the invention and are not to be construed in any way as limiting the scope of the invention.

EXAMPLE 1

Synthesis of 4-[N-(tert-butyl)-N-hydroxyamino]-N-thiazol-2-yl-benzamide (4)

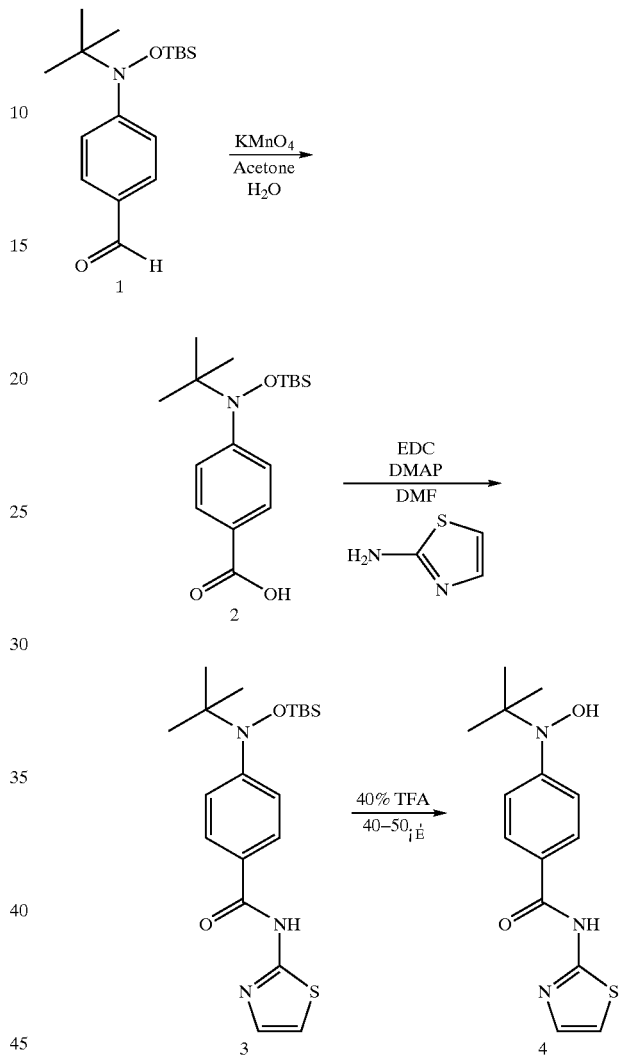

Step 1: Synthesis of 4-[N-(tert-butyl)-N-(tert-butyldimethylsilyloxy)amino]-benzoic acid (2)

2,2 g (7.15 mmol) of aldehyde 1 dissolved in acetone (10 mL) was slowly added to $H_2O$/acetone (21:3, v/v, 24 mL) solution containing 1.922 g (12.16 mmol) of $KMnO_4$, and the resulting mixture was stirred for 10 hours at room temperature. After completion of the reaction, it was filtered through a Celite pad and acetone was removed under reduced pressure. Aqueous phase was acidified with 1N HCl, extracted with $CH_2Cl_2$, dried over anhydrous $MgSO_4$, filtered and concentrated under reduced pressure. The residue was purified by flash column chromatography (silica, Hex:EtOAc=3:1) to give 1.97 g of compound 2 in 85% yield.

$^1$H NMR ($CDCl_3$): 7.73 (d, 2H, J=8.8 Hz), 7.40 (d, 2H, J=8.2 Hz), 1.12 (s, 9H) 0.92 (s, 9H), −0.13 (br s, 6H)

$^{13}$C NMR ($CDCl_3$): 172.1, 157.0, 129.7, 124.8, 61.9, 26.4, 26.2 18.0, −4.5

Step 2: Synthesis of 4-[N-(tert-butyl)-N-(tert-butyldimethylsilyloxy)amino]-N-thiazol-2-yl-benzamide (3)

To a solution of 3 g (9.27 mmol) of compound 2 in DMF (5 mL) were added 2.2 g (11.2 mmol) of 1-(3-dimethylamino)propyl-3-ethylcarbodiimide hydrochloride (EDC), 0.566 g (0.463 mmol) of 4-dimethylaminopyridine (DMAP), and 1.11 g (13.9 mmol) of 2-aminothiazole. After stirring for 24 hours at room temperature, H$_2$O and CH$_2$Cl$_2$ were added. The organic layer was separated, dried over anhydrous MgSO$_4$, filtered and concentrated under reduced pressure. The residue was purified by flash column chromatography (silica, Hex:EtOAc=5:1) to give 3.26 g of compound 3 in 87% yield.

$^1$H NMR (CDCl$_3$): 7.93 (d, 2H, J=8.7 Hz), 7.38 (d, 2H, J=8.1 Hz), 6.98 (d, 1H, J=3.7 Hz), 6.88 (d, 1H, J=3.6 Hz), 1.14 (s, 9H), 0.94 (s, 9H), −0.06 (br s, 6H)

$^{13}$C NMR (CDCl$_3$): 166.1, 160.9, 155.9, 137.1, 129.1, 127.8, 125.1, 113.2, 61.6, 26.3, 26.2, 18.0, −4.5

Step 3: Synthesis of 4-[N-(tert-butyl)-N-hydroxyamino]-N-thiazol-2-yl-benzamide (4)

A solution of 2.5 g (6.16 mmol) of compound 3 dissolved in 40% trifluoroacetic acid (TFA:H$_2$O:CH$_2$Cl$_2$=1:0.5:1, v/v) was stirred for 9 hours at 40–50° C. After completion of the reaction, 10 mL of water was added to quench the reaction. Ethyl acetate and sat'd NaHCO$_3$ solution were added to the mixture, and the organic layer was separated, dried over anhydrous MgSO$_4$, filtered and concentrated under reduced pressure. The residue was purified by flash column chromatography (silica, Hex:EtOAc=2:1) to give 1.5 g of compound 4 in 84% yield.

$^1$H NMR (DMSO-d$_6$): 12.45 (s, NH), 8.51 (s, OH), 8.01 (d, 2H, J=8.7 Hz), 7.54 (d, 1H, J=3.5 Hz), 7.32 (d, 2H, J=8.7 Hz), 7.25 (d, 1H, J=3.6 Hz), 1.12 (s, 9H)

$^{13}$C NMR (DMSO-d$_6$): 164.6, 158.8, 154.9, 137.5, 127.7, 126.9, 123.2, 113.63, 60.1, 26.2

EXAMPLE 2

Synthesis of 4-[N-(tert-butyl)-N-hydroxyamino]-N-pyridin-2-yl-benzamide (6)

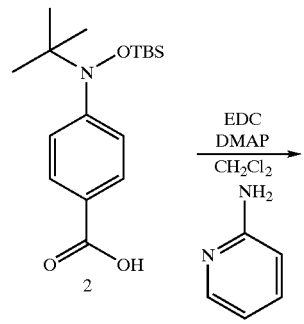

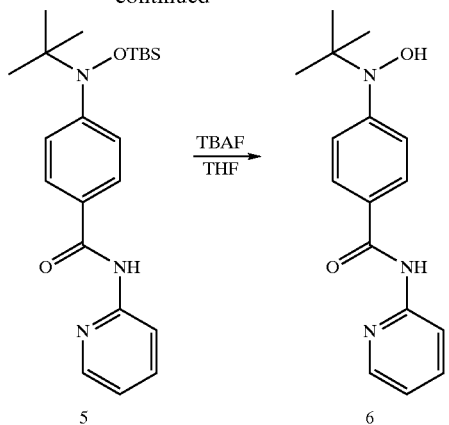

Step 1: Synthesis of 4-[N-(tert-butyl)-N-(tert-butyldimethylsilyloxy)amino]-N-pyridin-2-yl-benzamide (5)

To a solution of 1.0 g (3.09 mmol) of compound 2 in CH$_2$Cl$_2$ (5 mL) were added 0.733 g (3.71 mmol) of 1-(3-dimethylamino)propyl-3-ethylcarbodiimide hydrochloride, 0.189 g (1.545 mmol) of 4-dimethylaminopyridine, and 0.438 g (4.63 mmol) of 2-aminopyridine. After stirring for 12 hours at room temperature, H$_2$O and ethyl acetate were added. The organic layer was separated, washed with sat'd NaHCO$_3$ solution, dried over anhydrous MgSO$_4$, filtered and concentrated under reduced pressure. The residue was purified by flash column chromatography (silica, Hex:EtOAc=10:1) to give 2.3 g of compound 5 in 75% yield.

$^1$H NMR (CDCl$_3$): 8.58 (s, OH), 8.38 (d, 1H, J=8.3 Hz), 8.28 (s, 1H), 7.8 (d, 2H, J=8.0 Hz), 7.75 (t, 1H, J=8.4 Hz), 7.36 (d, 2H, J=8.3 Hz), 7.05 (t, 1H, J=5.5 Hz), 1.12 (s, 9H), 0.92 (s, 9H), −0.13 (br s, 6H)

$^{13}$C NMR (CDCl$_3$): 166.1, 155.3, 152.1, 147.8, 138.5, 130.6, 126.9, 125.1, 119.6, 114.5, 61.5, 26.3, 26.2, 18.0, −4.5

Step 2: Synthesis of 4-[N-(tert-butyl)-N-hydroxy-amino]-N-pyridin-2-yl-benzamide (6)

To a solution of 0.95 g (2.37 mmol) of compound 5 in THF (3 mL) was added 2.84 mL (2.84 mmol) of 1 M solution of tetrabutylammonium fluoride in THF at room temperature, and the solution was stirred for 1 hour. After completion of the reaction, 2 mL of water was added to quench the reaction. Ethyl acetate and sat'd NaHCO$_3$ solution were added to the mixture, and the organic layer was separated, dried over anhydrous MgSO$_4$, filtered and concentrated under reduced pressure. The residue was purified by flash column chromatography (silica, Hex:EtOAc=10:1) to give 0.44 g of compound 6 in 65% yield.

$^1$H NMR (DMSO-d$_6$): 10.58 (s, 1H), 8.47 (s, OH), 8.40 (s, 1H), 8.17 (d, 1H, J=8.4 Hz), 7.95 (d, 2H, J=8.4 Hz), 7.82 (t, 1H, J=7.1 Hz), 7.29 (d, 2H, J=8.2 Hz), 7.15 (t, 1H, J=5.7 Hz), 1.12 (s, 9H)

$^{13}$C NMR (DMSO-d$_6$): 164.7, 153.6, 151.5, 147.5, 137.6, 128.3, 126.9, 122.6, 119.1, 114.1, 59.2, 26.3

EXAMPLE 3

Synthesis of 4-[N-(tert-butyl)-N-hydroxyamino]-N-pyridin-2-yl-methyl-benzamide (8)

Step 1: Synthesis of 4-[N-(tert-butyl)-N-(tert-butyldimethylsilyloxy)amino]-N-pyridin-2-yl-methyl-benzamide (7)

To a solution of 0.15 g (0.464 mmol) of compound 2 in CH$_2$Cl$_2$ (10 mL) were added 0.11 g (0.561 mmol) of 1-(3-dimethylamino)propyl-3-ethylcarbodiimide hydrochloride, 0.03 g (0.232 mmol) of 4-dimethylaminopyridine, and 0.072 mL (0.695 mmol) of 2-aminomethylpyridine. After stirring for 2 hours at room temperature, H$_2$O and ethyl acetate were added. The organic layer was separated, dried over anhydrous MgSO$_4$, filtered and concentrated under reduced pressure. The residue was purified by flash column chromatography (silica, Hex:EtOAc=1:1) to give 0.13 g of compound 7 in 70% yield.

$^1$H NMR (CDCl$_3$): 8.55 (d, 1H, J=0.7 Hz), 7.75 (d, 2H, J=8.9 Hz), 7.67 (t, 1H, J=8.5 Hz), 7.58 (s, 1H), 7.32 (d, 2H, J=8.4 Hz), 7.27 (s, 1H), 7.19 (t, 1H, J=6.0 Hz), 4.74 (d, 2H, J=4.8 Hz), 1.08 (s, 9H), 0.89 (s, 9H), −0.14 (br s, 6H)

Step 2: Synthesis of 4-[N-(tert-butyl)-N-hydroxyamino]-N-pyridin-2-yl-methyl-benzamide (8)

To a solution of 0.06 g (0.145 mmol) of compound 7 in THF (1 mL) was added 0.73 mL (0.73 mmol) of 1 M solution of tetrabutylammonium fluoride in THF at room temperature, and the solution was stirred for 24 hours. After completion of the reaction, 2 mL of water was added to quench the reaction. Ethyl acetate and sat'd NH$_4$Cl solution were added to the mixture. The organic layer was separated, dried over anhydrous MgSO$_4$, filtered and concentrated under reduced pressure. The residue was purified by flash column chromatography (silica, Hex:EtOAc=1:2) to give 0.026 g of compound 8 in 60% yield.

$^1$H NMR (DMSO-d$_6$): 8.50 (d, 1H, J=3.9 Hz), 8.44 (s, 1H), 7.81 (d, 2H, J=8.3 Hz), 7.74 (t, 1H, J=7.2 Hz), 4.52 (d, 2H, J=5.5 Hz), 1.18 (s, 9H)

$^{13}$C NMR (DMSO-d$_6$): 166.0, 158.9, 153.7, 148.7, 136.6, 129.4, 126.6, 123.3, 121.9, 120.8, 59.8, 44.6, 26.1,

EXAMPLE 4

Synthesis of 4-[N-(tert-butyl)-N-hydroxyamino]-N-(8-hydroxyquinolin-5-yl)-benzamide (10)

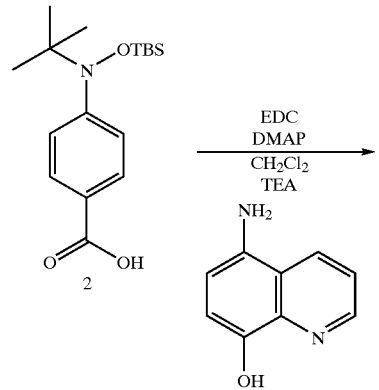

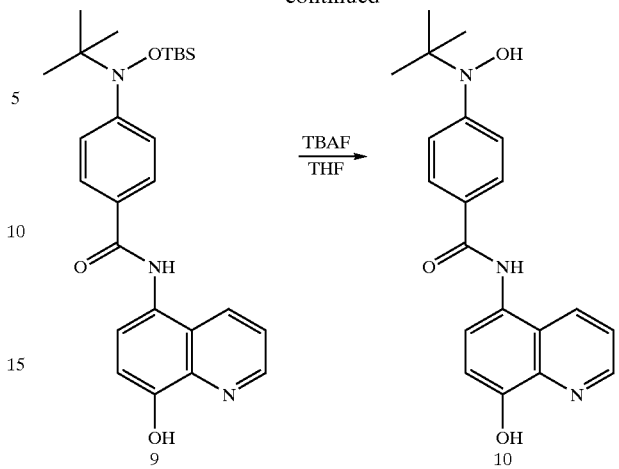

Step 1: Synthesis of 4-[N-(tert-butyl)-N-(tert-butyldimethylsilyloxy)amino]-N-(8-hydroxyquinolin-5-yl)-benzamide (9)

To a solution of 0.15 g (0.464 mmol) of compound 2 in CH$_2$Cl$_2$ (2 mL) were added 0.11 g (0.561 mmol) of 1-(3-dimethylamino)propyl-3-ethylcarbodiimide hydrochloride, 0.03 g (0.232 mmol) of 4-dimethylaminopyridine, 2 mL of triethylamine, and 0.16 g (0.695 mmol) of 5-amino-8-hydroxyquinoline HCl salt. After stirring for 24 hours at room temperature, H$_2$O and ethyl acetate were added. The organic layer was separated, dried over anhydrous MgSO$_4$, filtered and concentrated under reduced pressure. The residue was purified by flash column chromatography (silica, Hex:EtOAc=1:1) to give 0.076 g of compound 9 in 35% yield.

$^1$H NMR (CDCl$_3$): 8.86 (d, 1H, J=2.7 Hz), 8.20 (d, 2H, J=8.9 Hz), 8.16 (d, 1H, J=5 Hz) 7.35–7.32 (m, 2H), 6.75 (d, 1H, J=8.1 Hz)

Step 2: Synthesis of 4-[N-(tert-butyl)-N-hydroxyamino]-N-(8-hydroxyquinolin-5-yl)-benzamide (10)

To a solution of 0.04 g (0.085 mmol) of compound 9 in THF (1 mL) was added 0.43 mL (0.43 mmol) of 1 M solution of tetrabutylammonium fluoride in THF at room temperature, and the solution was stirred for 1 hour. After completion of the reaction, 2 mL of water was added to quench the reaction. Ethyl acetate and sat'd NH$_4$Cl solution were added to the mixture. The organic layer was separated, dried over anhydrous MgSO$_4$, filtered and concentrated under reduced pressure. The residue was purified by flash column chromatography (silica, Hex:EtOAc=10:1) to give 0.021 g of compound 10 in 70% yield.

$^1$H NMR (DMSO-d$_6$): 8.73 (d, 1H, J=2.9 Hz), 8.60 (s, 1H), 8.56 (s, 1H), 8.04 (d, 2H, J=8.3 Hz), 7.44 (s, 1H), 7.40 (d, 2H, J=8.0 Hz), 7.32 (d, 1H, J=8.1 Hz), 6.72 (d, 1H, J=8.1 Hz), 5.99 (s, OH), 1.16 (s, 9H)

Using the procedures described in the above Examples 1–4 and the appropriate starting materials and reagents, the following N-alkyl-N-phenylhydroxylamine compounds containing metal chelating groups could be prepared:

2-(N-tert-butyl-N-hydroxyamino)-N-furan-2-yl-benzamide
3-(N-tert-butyl-N-hydroxyamino)-N-furan-2-yl-benzamide
4-(N-tert-butyl-N-hydroxyamino)-N-furan-2-yl-benzamide
4-(N-cyclohexyl-N-hydroxyamino)-N-furan-2-yl-benzamide
4-(N-tert-butyl-N-acetoxyamino)-N-furan-2-yl-benzamide
4-(N-cyclohexyl-N-acetoxyamino)-N-furan-2-yl-benzamide 4-(N-tert-butyl-N-benzoyloxyamino)-N-furan-2-yl-benzamide
4-(N-cyclohexyl-N-benzoyloxyamino)-N-furan-2-yl-benzamide
4-(N-tert-butyl-N-hydroxyamino)-N-oxazol-2-yl-benzamide
4-(N-cyclohexyl-N-hydroxyamino)-N-oxazol-2-yl-benzamide
4-(N-tert-butyl-N-hydroxyamino)-N-thiophen-2-yl-benzamide
4-(N-cyclohexyl-N-hydroxyamino)-N-thiophen-2-yl-benzamide
2-(N-tert-butyl-N-hydroxyamino)-N-thiazol-2-yl-benzamide
3-(N-tert-butyl-N-hydroxyamino)-N-thiazol-2-yl-benzamide
4-(N-tert-butyl-N-hydroxyamino)-N-thiazol-2-yl-benzamide
4-(N-cyclohexyl-N-hydroxyamino)-N-thiazol-2-yl-benzamide
4-(N-tert-butyl-N-acetoxyamino)-N-thiazol-2-yl-benzamide
4-(N-cyclohexyl-N-acetoxyamino)-N-thiazol-2-yl-benzamide
4-(N-tert-butyl-N-benzoyloxyamino)-N-thiazol-2-yl-benzamide
4-(N-cyclohexyl-N-benzoyloxyamino)-N-thiazol-2-yl-benzamide
4-(N-tert-butyl-N-hydroxyamino)-N-(1H-imidazol-2-yl)-benzamide
4-(N-cyclohexyl-N-hydroxyamino)-N-(1H-imidazol-2-yl)-benzamide
4-(N-tert-butyl-N-hydroxyamino)-N-(1-methyl-1H-imidazol-2-yl)-benzamide
4-(N-cyclohexyl-N-hydroxyamino)-N-(1-methyl-1H-imidazol-2-yl)-benzamide
4-(N-tert-butyl-N-hydroxyamino)-N-(2H-pyrazol-3-yl)-benzamide
4-(N-cyclohexyl-N-hydroxyamino)-N-(2H-pyrazol-3-yl)-benzamide
4-(N-tert-butyl-N-hydroxyamino)-N-(2-methyl-2H-pyrazol-3-yl)-benzamide
4-(N-cyclohexyl-N-hydroxyamino)-N-(2-methyl-2H-pyrazol-3-yl)-benzamide
2-(N-tert-butyl-N-hydroxyamino)-N-pyridin-2-yl-benzamide
3-(N-tert-butyl-N-hydroxyamino)-N-pyridin-2-yl-benzamide
4-(N-tert-butyl-N-hydroxyamino)-N-pyridin-2-yl-benzamide
4-(N-cyclohexyl-N-hydroxyamino)-N-pyridin-2-yl-benzamide
4-(N-tert-butyl-N-acetoxyamino)-N-pyridin-2-yl-benzamide
4-(N-cyclohexyl-N-acetoxyamino)-N-pyridin-2-yl-benzamide
4-(N-tert-butyl-N-benzoyloxyamino)-N-pyridin-2-yl-benzamide
4-(N-cyclohexyl-N-benzoyloxyamino)-N-pyridin-2-yl-benzamide
4-(N-tert-butyl-N-hydroxyamino)-N-pyrimidin-2-yl-benzamide
4-(N-cyclohexyl-N-hydroxyamino)-N-pyrimidin-2-yl-benzamide
4-(N-tert-butyl-N-hydroxyamino)-N-pyridazin-3-yl-benzamide
4-(N-cyclohexyl-N-hydroxyamino)-N-pyridazin-3-yl-benzamide
4-(N-tert-butyl-N-hydroxyamino)-N-pyrazin-2-yl-benzamide
4-(N-cyclohexyl-N-hydroxyamino)-N-pyrazin-2-yl-benzamide
4-(N-tert-butyl-N-hydroxyamino)-N-[1,3,5]triazin-2-yl-benzamide
4-(N-cyclohexyl-N-hydroxyamino)-N-[1,3,5]triazin-2-yl-benzamide
4-(N-tert-butyl-N-hydroxyamino)-N-(2H-[1,2,4]triazol-3-yl)-benzamide
4-(N-cyclohexyl-N-hydroxyamino)-N-(2H-[1,2,4]triazol-3-yl)-benzamide
4-(N-tert-butyl-N-hydroxyamino)-N-(2-methyl-2H-[1,2,4]triazol-3-yl)-benzamide
4-(N-cyclohexyl-N-hydroxyamino)-N-(2-methyl-2H-[1,2,4]triazol-3-yl)-benzamide
4-(N-tert-butyl-N-hydroxyamino)-N-(1H-tetrazol-5-yl)-benzamide
4-(N-cyclohexyl-N-hydroxyamino)-N-(1H-tetrazol-5-yl)-benzamide
4-(N-tert-butyl-N-hydroxyamino)-N-(1-methyl-1H-tetrazol-5-yl)-benzamide
4-(N-cyclohexyl-N-hydroxyamino)-N-(1-methyl-1H-tetrazol-5-yl)-benzamide

EXAMPLE 5

Inhibition of Lipid Peroxidation

The compounds of the present invention were tested for antioxidant effect in terms of the repression of the radical chain reaction of a multilayer liposome.

The liposome was prepared as followings: 30 mg of commercially available soybean phosphatidylcholine (PC, Sigma Chemical Co., U.S.A.) was dissolved in 1 mL of ethanol, and 200 $\mu$L of the ethanol/PC solution was added to 10 mL of 10 mM Tris buffer including 50 mM NaCl (pH 7.0) with stirring.

The ability of a compound to inhibit oxidation of the liposome was evaluated as followings: To 400 $\mu$L of the liposomes were added the test compound (in buffer or ethanol) and histidine-$FeCl_3$ (167:33 $\mu$M final). Oxidation was initiated by the addition of $FeCl_2$ (33 $\mu$M final prepared in nitrogen purged water). The mixtures was shaken at 37° C. for 15 minutes. Thereafter, tubes were treated with 1 mL of 0.67% thiobabituric acid (TBA):10% trichloroacetic acid (2:1, v/v) in 0.25 N HCl solution, containing 1.5% (v/v) t-butylhydroxytoluene (BHT) to terminate oxidation. The aliquots were heated to 100° C. for 20 minutes. After ice cooling, 1 mL of chloroform was added to 1 mL supernatant from tubes and tubes were centrifuged. The absorbances of the resulting supernatant were measured at 532 nm (see: Table 1 below).

TABLE 1

| | Inhibitor Concentration ($IC_{50}$) |
|---|---|
| Example 1 | 1.44 $\mu$M |
| Example 2 | 4.30 $\mu$M |
| Example 3 | 11.05 $\mu$M |
| Example 4 | 61.85 $\mu$M |
| Ebselen | 68.86 $\mu$M |
| Trolox | 10.25 $\mu$M |

It can be seen from Table 1 that the compounds of the invention have similar or superior LPO inhibition activity to the reference compounds, Trolox (vitamin E derivative, used as a reference material in numerous in vitro and in vivo antioxidant test) and Ebselen (the most promising antioxidant currently and is in clinical phase III).

EXAMPLE 6

Protection of Neuron Cells by the Compounds of the Invention

Example 6-1

The Culture of Neuron Cells of Cerebral Cortex

Mixed cortical cell cultures, containing both neuronal and glial elements, were prepared from fetal ICR (Institute Cancer Research) mice at 14–15 days of gestation. Briefly, dissociated cortical cells were plated onto previously established glial monolayer culture at 2.5 hemispheres per 24-multiwell plate (Nunc, U.S.A.). The plating medium consisted of Eagle's minimal essential medium (Earle's salts, supplied glutamine-free) supplemented with glucose (final concentration, 20 mM), 2 mM glutamine, 5% fetal bovine serum, and 5% horse serum. Ten mM cytosine arabinoside was added to the medium 5–6 days after the plating to halt the growth of non-neuronal cells. Cultures were maintained at 37° C. in a humidified $CO_2$ incubator (5%) and used for experiments after between 10–14 days in vitro (DIV).

The glial feeder cultures were prepared from neocortices of postnatal (1–3 day-old) mice. Dissociated cortical cells were plated at 0.25 hemispheres per 24-multiwell plate, in plating medium supplemented with 5% fetal bovine serum, and 10% horse serum. With this method, most neurons do not survive, but astrocytes do, resulting in astrocyte-rich cultures. Glial cultures were grown to confluency for 10–30 days, when they were used to generate mixed cortical cultures.

Example 6-2

Protection of Cortical Neuronal Cell Death Induced by $Fe^{2+}$ Ion and $Zn^{2+}$ Ion When ferrous iron is placed in normoxic solution, it autooxidizes to produce ROS in the form of hydroxyl radicals, superoxide anion free radicals, and hydrogen peroxide.

Cortical cell cultures prepared in Example 6-1 were exposed for 24 hours to 30 $\mu$M $FeCl_2$ (Fe) or 35 $\mu$M $ZnCl_2$ (Zn, neuro-excitotoxic factor), to induce neuronal cell death. Twenty four hour exposure to toxin with or without test compounds was done in serum free Eagle's minimal essential medium (MEM) supplemented with 20 mM glucose and 38 mM sodium bicarbonate in 5% $CO_2$ incubator at 37° C. All of compounds were dissolved in DMSO at high concentrations, and then diluted to final concentrations in the exposure medium at the time of addition.

Methods of measuring cell death were as follows:

Overall cell injury was first estimated in all experiments by examination of cultures under phase-contrast microscope. The morphological assessments were usually performed one day after exposure to toxins, at which point the process of cell death was largely completed.

In addition, overall neuronal cell injury was quantitatively estimated by measuring the activity of lactate dehydrogenase (LDH), released by damaged or destroyed cells, into the extracellular fluid. A small amount of LDH was always present in the media of cultures that underwent the same exposure procedures but without the addition of toxins (sham wash controls). This background amount, determined on sister sham wash controls within each experiment, was subtracted from values obtained in toxin-treated cultures. The absolute value of the LDH efflux produced by toxin exposure was quite consistent within sister cultures of single plating, but varied somewhat in cultures of different platings. This variability is largely a function of resultant neuronal density (which varied in spite of constant original plating densities, presumably reflecting small variations in cell preparation or serum characteristics). Therefore, each LDH value was scaled to the maximal neuronal LDH release (=100) after 24 hours exposure to 30 $\mu$M $FeCl_2$ (Fe) or 35 $\mu$M $ZnCl_2$ (Zn), in sister cultures, where near complete neuronal death with no glial damage occurs. Numbers greater than 100 usually indicate additional astroglial cell injury.

FIG. 1-a is a graph showing the results of combined treatment of Trolox and $Fe^{2+}$ toxin.

FIG. 1-b is a graph showing the results of combined treatment of Trolox and $Zn^{2+}$ toxin.

FIG. 2-a is a graph showing the results of combined treatment of compound obtained in Example 1 and $Fe^{2+}$ toxin.

FIG. 2-b is a graph showing the results of combined treatment of compound obtained in Example 1 and $Zn^{2+}$ toxin.

FIG. 3-a is a graph showing the results of combined treatment of compound obtained in Example 2 and $Fe^{2+}$ toxin.

FIG. 3-b is a graph showing the results of combined treatment of compound obtained in Example 2 and $Zn^{2+}$ toxin.

FIG. 4-a is a graph showing the results of combined treatment of compound obtained in Example 3 and $Fe^{2+}$ toxin.

FIG. 4-b is a graph showing the results of combined treatment of compound obtained in Example 3 and $Zn^{2+}$ toxin.

FIG. 5-a is a graph showing the results of combined treatment of compound obtained in Example 4 and $Fe^{2+}$ toxin.

FIG. 5-b is a graph showing the results of combined treatment of compound obtained in Example 4 and $Zn^{2+}$ toxin.

As can be seen in FIGS. 1-a to 5-b, it was clearly demonstrated that the compounds of the invention effectively protected the neuronal cell injury induced by $Fe^{2+}$ or $Zn^{2+}$ toxin, assuring that they can be used as neuroprotective agents in order to protect cerebral neuron cells from ROS and/or excess Zn ions (neuro-excitotoxic factor).

EXAMPLE 7

Toxicity of the Compounds on the Neuron Cells

The viability of cortical cell prepared in Example 6-1 was quantified by lactate dehydrogenase (LDH) assay after exposure for 24 hours to the different concentrations of the test compound. Twenty-four hours exposure to the compound was done in serum free Eagle's minimal essential medium (MEM) supplemented with 20 mM glucose and 38 mM sodium bicarbonate in 5% $CO_2$ incubator at 37° C. All of compounds were dissolved in DMSO at high concentrations, and then diluted to final concentrations in the exposure medium at the time of addition.

Measurement of cell death was the same as the method in Example 6-2.

FIG. 6 is a graph showing the level of cell damage as the treatment concentration of Trolox increases.

Figure 7:
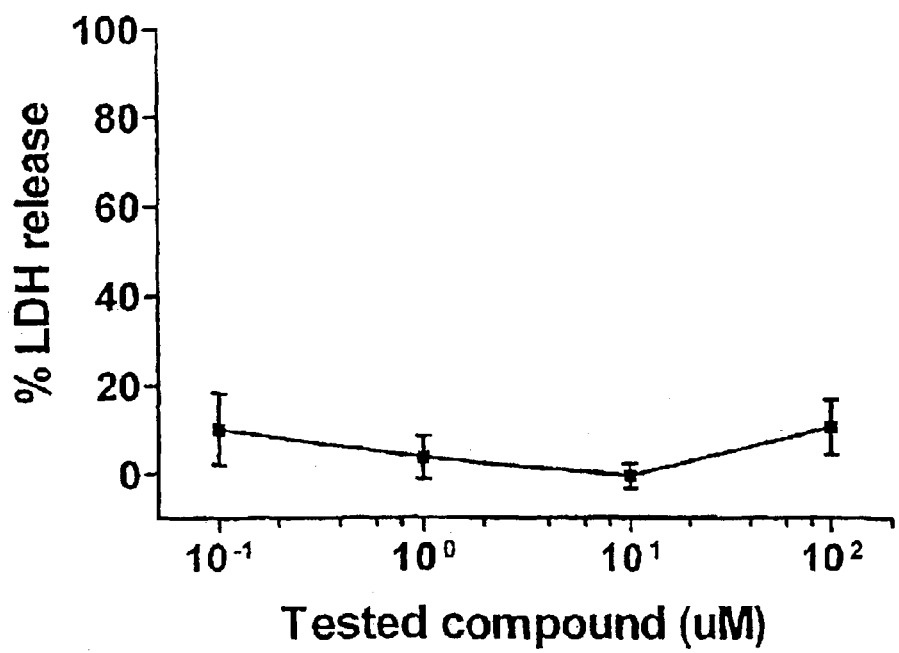
FIG. 7 is a graph showing the level of cell damage as the treatment concentration of compound obtained in Example 1 increases.

FIG. 7 is a graph showing the level of cell damage as the treatment concentration of compound obtained in Example 1 increases.

Figure 8:
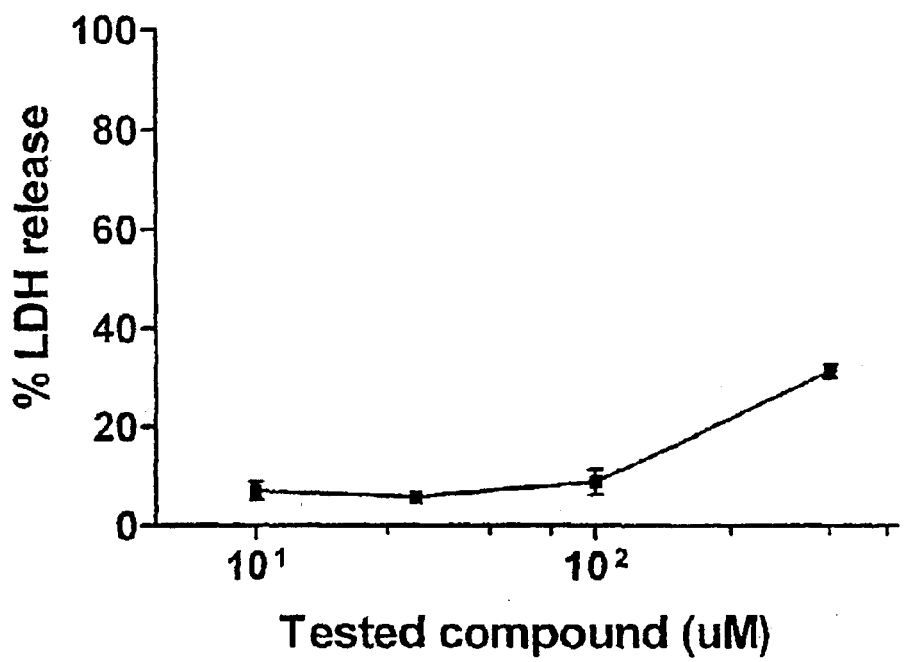
FIG. 8 is a graph showing the level of cell damage as the treatment concentration of compound obtained in Example 2 increases.

FIG. 8 is a graph showing the level of cell damage as the treatment concentration of compound obtained in Example 2 increases.

Figure 9:
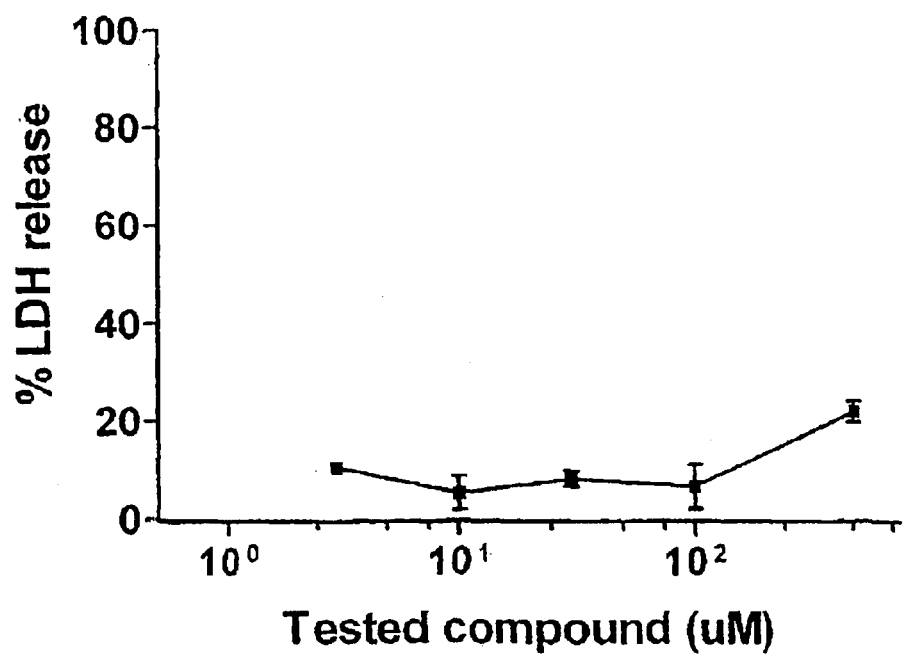
FIG. 9 is a graph showing the level of cell damage as the treatment concentration of compound obtained in Example 3 increases.

FIG. 9 is a graph showing the level of cell damage as the treatment concentration of compound obtained in Example 3 increases.

Figure 10:
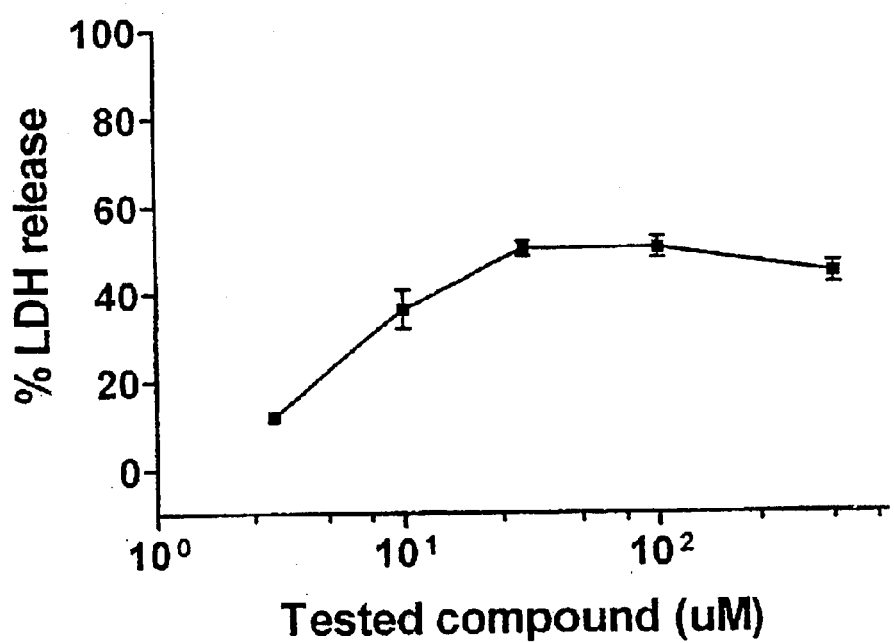
FIG. 10 is a graph showing the level of cell damage as the treatment concentration of compound obtained in Example 4 increases.

FIG. 10 is a graph showing the level of cell damage as the treatment concentration of compound obtained in Example 4 increases.

As seen in FIGS. 6 to 10, the compounds of the invention exhibit low cytotoxicity, assuring that they can be administered at large doses in a safe manner.

EXAMPLE 8

Protection of Cell Damage by Ischemia (In Vivo)

Male Mongolian gerbils (*Meriones unguiculatus*) weighing 80–88 g were used in the present study. Each animal was medicated P.O. with vehicle, Ebselen or various test compounds (60 mg/kg in 10% DMSO), after 30 minutes ischemic injury, respectively. 20 animals were allotted into every group. The animals were placed under general anesthesia with a mixture of 2.5% isoflurane in 33% oxygen and 67% nitrous oxide. A midline ventral incision was made in the neck. Both common carotid arteries were isolated, freed of nerve fibers, and occluded using nontraumatic aneurysm clips. Complete interruption of blood flow was confirmed by observing the central artery in eyeballs using ophthalmoscope. After five minutes of occlusion, the aneurysm clips were removed from both common carotid arteries. Restoration of blood flow (reperfusion) was observed directly under the microscope. Sham-operated controls were subjected to the same surgical procedures except that common carotid arteries were not occluded. Body temperature was monitored and maintained at 37° C.±0.5° C. during surgery and during the immediate postoperative period until the animals recovered fully from anesthesia. At the designated reperfusion time (4 days), operated animals and sham animals were killed.

Animals were perfused transcardially with phosphate-buffered saline (PBS, pH 7.4) followed by 4% paraformaldehyde in 0.1M phosphate buffer (pH 7.4) at 4 days (n=7) after surgery. The brains were removed, and postfixed in the same fixative for 4 hours. The brain tissues were cryoprotected by infiltration with 30% sucrose overnight. Cornoy fixed specimens were cut into 30 sections on a cryostat. The sections were sequentially stained by Cresyl violet dye.

Images of staining in the hippocampus of each animal were captured with an Applescanner. The brightness and contrast of each image file were uniformly enhanced by Adobe Photoshop version 2.4.1, followed by analysis using NIH Image 1.59 software. All data obtained from the quantitative data were analyzed using one-way ANOVA to determine statistical significance. Bonferroni's test was used for post-hoc comparisons. P values below 0.05 or 0.01 were considered statistically significant.

FIG. 11-*a* is a graph showing the protection level of cell damage in case of the treatment of the compound of the invention after ischemia.

FIG. 11-*b* is a photomicrograph showing the protection level of cell damage in case of the treatment of the compound of the invention after ischemia.

As the results, the test compound prepared in Example 1 has more neuroprotective effects against ischemic neuronal degeneration than those of Ebselen. The compound synthesized in Example 1 showed that the protective effect was 81% in post-treated groups. In the Ebselen-treated groups, the effect was 59%.

In conclusion, we suggest that the compound prepared in Example 1 may be a candidate as a treatment drug against ischemia.

As described in detail and illustrated above, this invention provides novel N-alkyl-N-phenylhydroxylamine compounds containing metal chelating groups, a process for producing the same, the use of said novel compounds as therapeutics for treating and/or preventing various medical diseases arising from ROS and/or excess Zn ions. The compounds of the invention possess similar or superior LPO inhibition activity to the reference compounds of Trolox and Ebselen. While showing lower toxicity, they also effectively inhibit the cerebral neuronal cell death caused by ROS and/or zinc ion, and show neuroprotective effects against ischemic neuronal degeneration.

From the foregoing description, various modifications and changes in the compositions and methods of this invention will occur to those skilled in the art. All such modifications coming within the scope of the appended claims are intended to be included therein.

What is claimed is:

1. A chemical compound with the following formula (I), and pharmaceutically acceptable salts thereof:

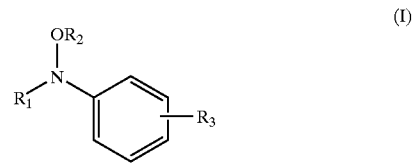

(I)

wherein $R_1$ denotes branched alkyl, aralkyl, aryl or substituted aryl;

wherein $R_2$ denotes hydrogen, or $COR_6$, wherein $R_6$ is alkyl or aryl; and wherein $R_3$ denotes $CO_2H$, $CONH_2$, or $CONR_4R_5$, wherein $R_4$ denotes hydrogen, alkyl or aryl, wherein $R_5$ denotes an unsaturated or saturated heterocyclic radical having 1 to 4 heteroatoms selected from the group consisting of nitrogen, oxygen and sulfur, wherein the heterocyclic radical is selected from the group consisting of furanyl, oxazolyl, isooxazolyl, thiophenyl, thiazolyl, isothiazolyl, pyrrolyl, imidazolyl, pyrazolyl, oxadiazolyl, thiadiazoyl, pyridyl, pyrimidinyl, pyrazinyl, pyridazinyl, triazinyl, triazolyl, and tetrazolyl, and wherein the heterocyclic radical is substituted or unsubstituted with one or two, identical or different substituent groups selected from the group consisting of halogen, $C_{1-2}$-alkyl, $C_{1-4}$-alkoxy, $C_{1-4}$-alkylthio, hydroxy, mercapto, trifluoromethyl, nitro, phenyl, nitrile, carboxy or $C_{1-4}$-alkoxycarbonyl.

2. A chemical compound with the following formula (II), and pharmaceutically acceptable salts thereof:

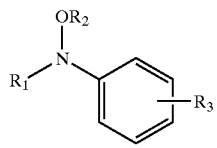

(II)

wherein $R_1$ is selected from the group consisting of branched $C_{3-8}$-alkyl, $C_{5-8}$-cycloalkyl and aryl;

wherein $R_2$ is selected from the group consisting of hydrogen, straight or branched $C_{1-18}$-alkyl carbonyl, benzoyl, and substituted benzoyl substituted with one to three, identical or different substituent groups selected from the group consisting of halogen, $C_{1-4}$-alkyl, $C_{1-4}$-alkoxy, hydroxy, trifluoromethyl, nitro, nitrile, carboxy, alkoxycarbonyl, alkoxycarbonylalkyl and methylenedioxy; and wherein $R_3$ is selected from the group consisting of $CO_2H$, $CONH_2$, and amides $CONR_4R_5$, wherein $R_4$ represents hydrogen, $C_{1-4}$-alkyl, aralkyl or cycloalkyl, wherein $R_5$ denotes unsaturated or saturated heterocyclic radical having 1 to 4 heteroatoms selected from the group consisting of nitrogen, oxygen and sulfur, wherein the heterocyclic radical is selected from the group consisting of furanyl, oxazolyl, isooxazolyl, thiophenyl, thiazolyl, isothiazolyl, pyrrolyl, imidazolyl, pyrazolyl, oxadiazoyl, thiadiazoyl, pyridyl, pyrimidinyl, pyrazinyl, pyridazinyl, triazinyl, triazolyl, and tetrazolyl, and wherein the heterocyclic radical is substituted or unsubstituted with one or two, identical or different substituent groups selected from the group consisting of halogen, $C_{1-2}$-alkyl, $C_{1-4}$-alkoxy, $C_{1-4}$-alkylthio, hydroxy, mercapto, trifluoromethyl, nitro, phenyl, nitrile, carboxy and $C_{1-4}$-alkoxycarbonyl.

3. The compound according to claim 2,
wherein $R_1$ is selected from the group consisting of isopropyl, tert-butyl, cyclopentyl, cyclohexyl and phenyl;
wherein $R_2$ is selected from the group consisting of hydrogen, acetyl, propionyl and benzoyl; and
wherein $R_4$ represents hydrogen, methyl, ethyl, propyl, benzyl, cyclopentyl or cyclohexyl; and
wherein the heterocyclic radical is selected from the group consisting of oxazolyl, thiazolyl, isothiazolyl, imidazolyl, pyrazolyl, thiadiazoyl, pyridyl, pyrimidinyl, pyrazinyl, pyridazinyl, triazinyl, triazolyl, and tetrazolyl, and wherein the substituent group of the substituted heterocyclic radical is selected from the group consisting of fluorine, chloride, bromine, methyl, methoxy, ethoxy, methylmercapto, hydroxy, mercapto, trifluoromethyl, nitro, phenyl, nitrile, carboxy, methoxycarbonyl, and ethoxycarbonyl.

4. A process for preparing a compound of the formula (I) or a salt thereof as defined in claim 1, the process comprising:
(i) oxidizing an O-protected compound (1) to give a compound represented by formula (2);
(ii) amide-coupling the compound of formula (2) with $HNR_4R_5$ to provide a compound represented by formula (3);
(iii) deprotecting the oxygen from the compound of formula (3) to provide a compound represented by formula (4); and
(iv) conducting O-acylation of N-hydroxy group of the compound of formula (4) to produce N-acylhydroxy group.

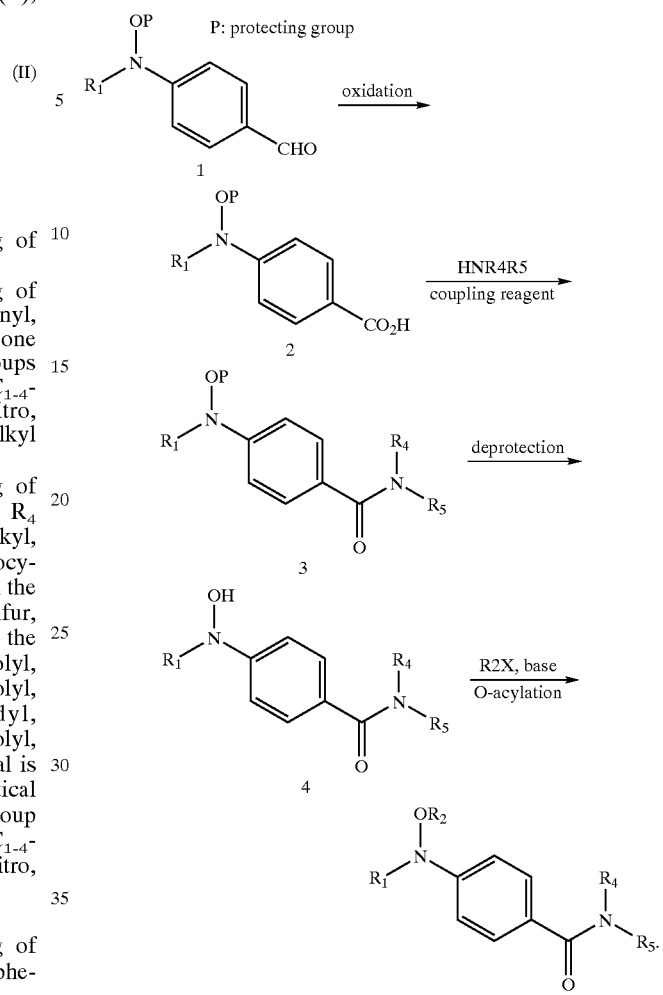

5. A pharmaceutical composition useful as an antioxidant and/or a metal chelating agent which comprises as an active ingredient an effective amount of the compound of formula (I) defined in claim 1, in combination with one or more pharmaceutically acceptable carriers or excipients.

6. A neuroprotective agent comprising as an active ingredient an effective amount of the compound of formula (I) defined in claim 1, in combination with one or more pharmaceutically acceptable carriers or excipients.

7. The pharmaceutical composition according to claim 6 wherein the carrier is an oral carrier.

8. The pharmaceutical composition according to claim 6 wherein the carrier is an injectable carrier.

9. A method for treating a living body afflicted with a condition in need of an antioxidant and/or a metal chelating agent, the method comprising administering to the living body an amount of the compound of formula (I) defined in claim 1 which is effective for alleviation of said condition.

10. A method for treating a living body with an acute or progressive neurodegenerative disorder or disease, the method comprising administering to the living body an amount of the compound of formula (I) defined in claim 1 which is effective for alleviation of said disease or disorder.

11. The method according to claim 10, wherein the acute or progressive neurodegenerative disease or disorder is selected from the group consisting of stroke, Parkinson's disease and Alzheimer's disease.

12. The method according to claim 11, wherein the living body exhibits a symptom of stroke.

13. The compound of claim 1, wherein $R_1$ is selected from the group consisting of isopropyl, tert-butyl and phenyl.

14. The compound of claim 1, wherein $R_2$ is selected from the group consisting of hydrogen, acetyl, propionyl and benzoyl.

15. The compound of claim 1, wherein $R_4$ represents hydrogen, methyl, ethyl and propyl.

16. The compound of claim 1, wherein the heterocyclic radical is selected from the group consisting of oxazolyl, thiazolyl, isothiazolyl, imidazolyl, pyrazolyl, thiadiazoyl, pyridyl, pyrimidinyl, pyrazinyl, pyridazinyl, triazinyl, triazolyl and tetrazolyl.

17. The compound of claim 1, wherein the compound is represented by the following formula:

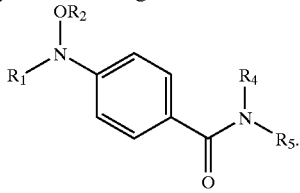

18. A chemical compound and pharmaceutically acceptable salts thereof, wherein the chemical compound is selected from the group consisting of:

2-(N-tert-butyl-N-hydroxyamino)-N-(furan-2-yl)-benzamide;
3-(N-tert-butyl-N-hydroxyamino)-N-(furan-2-yl)-benzamide;
4-(N-tert-butyl-N-hydroxyamino)-N-(furan-2-yl)-benzamide;
4-(N-cyclohexyl-N-hydroxyamino)-N-(furan-2-yl)-benzamide;
4-(N-tert-butyl-N-acetoxyamino)-N-(furan-2-yl)-benzamide;
4-(N-cyclohexyl-N-acetoxyamino)-N-(furan-2-yl)-benzamide;
4-(N-tert-butyl-N-benzoyloxyamino)-N-(furan-2-yl)-benzamide;
4-(N-cyclohexyl-N-benzoyloxyamino)-N-(furan-2-yl)-benzamide;
4-(N-tert-butyl-N-hydroxyamino)-N-(oxazol-2-yl)-benzamide;
4-(N-cyclohexyl-N-hydroxyamino)-N-(oxazol-2-yl)-benzamide;
4-(N-tert-butyl-N-hydroxyamino)-N-(thiophen-2-yl)-benzamide;
4-(N-cyclohexyl-N-hydroxyamino)-N-(thiophen-2-yl)-benzamide;
2-(N-tert-butyl-N-hydroxyamino)-N-(thiazol-2-yl)-benzamide;
3-(N-tert-butyl-N-hydroxyamino)-N-(thiazol-2-yl)-benzamide;
4-(N-tert-butyl-N-hydroxyamino)-N-(thiazol-2-yl)-benzamide;
4-(N-cyclohexyl-N-hydroxyamino)-N-(thiazol-2-yl)-benzamide;
4-(N-tert-butyl-N-acetoxyamino)-N-(thiazol-2-yl)-benzamide;
4-(N-cyclohexyl-N-acetoxyamino)-N-(thiazol-2-yl)-benzamide;
4-(N-tert-butyl-N-benzoyloxyamino)-N-(thiazol-2-yl)-benzamide;
4-(N-cyclohexyl-N-benzoyloxyamino)-N-(thiazol-2-yl)-benzamide;
4-(N-tert-butyl-N-hydroxyamino)-N-(1H-imidazol-2-yl)-benzamide;
4-(N-cyclohexyl-N-hydroxyamino)-N-(1H-imidazol-2-yl)-benzamide;
4-(N-tert-butyl-N-hydroxyamino)-N-(1-methyl-1H-imidazol-2-yl)-benzamide;
4-(N-cyclohexyl-N-hydroxyamino)-N-(1-methyl-1H-imidazol-2-yl)-benzamide;
4-(N-tert-butyl-N-hydroxyamino)-N-(2H-pyrazol-3-yl)-benzamide;
4-(N-cyclohexyl-N-hydroxyamino)-N-(2H-pyrazol-3-yl)-benzamide;
4-(N-tert-butyl-N-hydroxyamino)-N-(2-methyl-2H-pyrazol-3-yl)-benzamide;
4-(N-cyclohexyl-N-hydroxyamino)-N-(2-methyl-2H-pyrazol-3-yl)-benzamide;
2-(N-tert-butyl-N-hydroxyamino)-N-(pyridin-2-yl)-benzamide;
3-(N-tert-butyl-N-hydroxyamino)-N-(pyridin-2-yl)-benzamide;
4-(N-tert-butyl-N-hydroxyamino)-N-(pyridin-2-yl)-benzamide;
4-(N-cyclohexyl-N-hydroxyamino)-N-(pyridin-2-yl)-benzamide;
4-(N-tert-butyl-N-acetoxyamino)-N-(pyridin-2-yl)-benzamide;
4-(N-cyclohexyl-N-acetoxyamino)-N-(pyridin-2-yl)-benzamide;
4-(N-tert-butyl-N-benzoyloxyamino)-N-(pyridin-2-yl)-benzamide;
4-(N-cyclohexyl-N-benzoyloxyamino)-N-(pyridin-2-yl)-benzamide;
4-(N-tert-butyl-N-hydroxyamino)-N-(pyrimidin-2-yl)-benzamide;
4-(N-cyclohexyl-N-hydroxyamino)-N-(pyrimidin-2-yl)-benzamide;
4-(N-tert-butyl-N-hydroxyamino)-N-(pyridazin-3-yl)-benzamide;
4-(N-cyclohexyl-N-hydroxyamino)-N-(pyridazin-3-yl)-benzamide;
4-(N-tert-butyl-N-hydroxyamino)-N-(pyrazin-2-yl)-benzamide;
4-(N-cyclohexyl-N-hydroxyamino)-N-(pyrazin-2-yl)-benzamide;
4-(N-tert-butyl-N-hydroxyamino)-N-([1,3,5]triazin-2-yl)-benzamide;
4-(N-cyclohexyl-N-hydroxyamino)-N-([1,3,5]triazin-2-yl)-benzamide;
4-(N-tert-butyl-N-hydroxyamino)-N-(2H-[1,2,4]triazol-3-yl)-benzamide;
4-(N-cyclohexyl-N-hydroxyamino)-N-(2H-[1,2,4]triazol-3-yl)-benzamide;
4-(N-tert-butyl-N-hydroxyamino)-N-(2-methyl-2H-[1,2,4]triazol-3-yl)-benzamide;
4-(N-cyclohexyl-N-hydroxyamino)-N-(2-methyl-2H-[1,2,4]triazol-3-yl)-benzamide;
4-(N-tert-butyl-N-hydroxyamino)-N-(1H-tetrazol-5-yl)-benzamide;
4-(N-cyclohexyl-N-hydroxyamino)-N-(1H-tetrazol-5-yl)-benzamide;
4-(N-tert-butyl-N-hydroxyamino)-N-(1-methyl-1H-tetrazol-5-yl)-benzamide; and
4-(N-cyclohexyl-N-hydroxyamino)-N-(1-methyl-1H-tetrazol-5-yl)-benzamide.

19. A pharmaceutical composition useful as an antioxidant and/or a metal chelating agent, the composition comprising: an effective amount the compound of claim 18 and one or more pharmaceutically acceptable carriers or excipients.

20. A neuroprotective agent comprising: an effective amount of the compound of claim 18 and one or more pharmaceutically acceptable carriers or excipients.

21. A method for treating a living body afflicted with a condition in need of an antioxidant and/or a metal chelating agent, the method comprising administering to the living body the compound of claim 18 in an amount effective for alleviation of said condition.

22. A method of treating a living body with an acute or progressive neurodegenerative disorder or disease, the method comprising administering to the living body the compound of claim 18 in amount effective for alleviation of the disorder or disease.

23. A process for preparing a compound of the formula (I) or a salt thereof as defined in claim 2, the process comprising:
   (i) oxidizing an O-protected compound (1) to give a compound represented by formula (2);
   (ii) amide-coupling the compound of formula (2) with $HNR_4R_5$ to provide a compound represented by formula (3);
   (iii) deprotecting the oxygen from the compound of formula (3) to provide a compound represented by formula (4); and
   (iv) conducting O-acylation of N-hydroxy group of the compound of formula (4) to produce N-acylhydroxy group

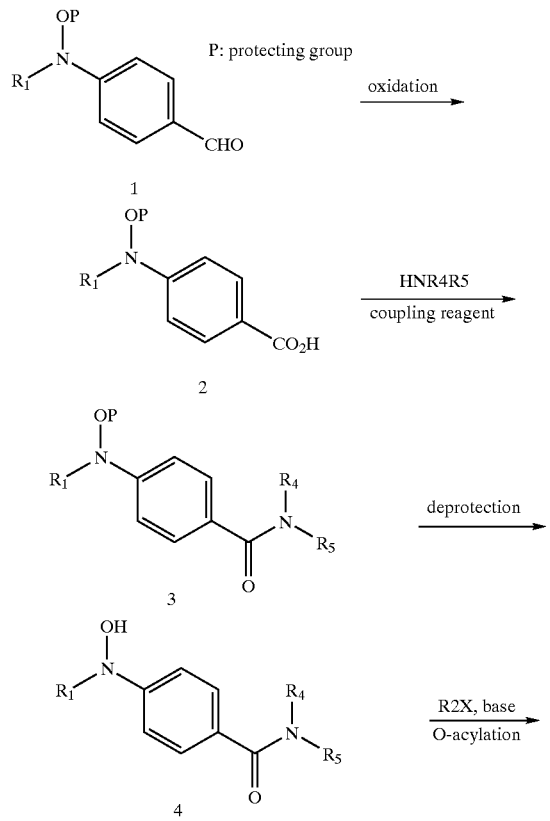

24. A pharmaceutical composition useful as an antioxidant and/or a metal chelating agent which comprises an effective amount of the compound of formula (II) defined in claim 2, in combination with one or more pharmaceutically acceptable carriers or excipients.

25. A neuroprotective agent comprising an effective amount of the compound of formula (II) defined in claim 2, in combination with one or more pharmaceutically acceptable carriers or excipients.

26. The pharmaceutical composition according to claim 25, wherein the carrier is an oral carrier.

27. The pharmaceutical composition according to claim 25, wherein the carrier is an injectable carrier.

28. A method for treating a living body afflicted with a condition in need of an antioxidant and/or a metal chelating agent, the method comprising administering to the living body the compound of formula (II) defined in claim 2 in an amount effective for alleviation of said condition.

29. A method of treating a living body with an acute or progressive neurodegenerative disorder or disease, the method comprising administering to the living body the compound of formula (II) defined in claim 2 in an amount effective for alleviation of said disease or disorder.

30. The method according to claim 29, wherein the acute or progressive neurodegenerative disease or disorder is selected from the group consisting of stroke, Parkinson's disease and Alzheimer's disease.

31. The method according to claim 30, wherein the living body exhibits a symptom of stroke.

32. The compound of claim 2, wherein $R_1$ is selected from the group consisting of cyclopentyl, cyclohexyl and phenyl.

33. The compound of claim 2, wherein $R_2$ is selected from the group consisting of hydrogen, acetyl, propionyl and benzoyl.

34. The compound of claim 2, wherein $R_4$ represents hydrogen, methyl, ethyl, propyl, benzyl, cyclopentyl and cyclohexyl.

35. The compound of claim 2, wherein the heterocyclic radical is selected from the group consisting of oxazolyl, thiazolyl, isothiazolyl, imidazolyl, pyrazolyl, thiadiazoyl, pyridyl, pyrimidinyl, pyrazinyl, pyridazinyl, triazinyl, triazolyl and tetrazolyl.

36. The compound of claim 2, wherein the compound is represented by the following formula:

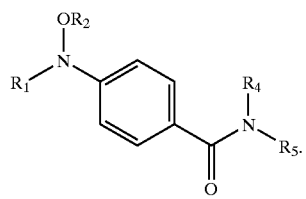

* * * * *

UNITED STATES PATENT AND TRADEMARK OFFICE
CERTIFICATE OF CORRECTION

PATENT NO. : 6,949,654 B2
APPLICATION NO. : 10/456024
DATED : September 27, 2005
INVENTOR(S) : Oh et al.

It is certified that error appears in the above-identified patent and that said Letters Patent is hereby corrected as shown below:

On the cover page of the patent, at the 2nd line below "OTHER PUBLICATIONS", please replace "(abstact)" with -- (abstract) --.

On the cover page, at the 13th line below "OTHER PUBLICATIONS", after "as" please insert -- a --.

On the cover page, at the 17th line below "OTHER PUBLICATIONS", please replace "Gerebral" with -- Cerebral --.

At sheet 1 of 9, Fig. 1-b, please replace "T.oxin" with -- Toxin --.

At sheet 3 of 9, Fig. 3-b, please replace "compounde" with -- compound--.

At column 2, line 44, please replace "et al," with -- et al., --.

At column 2, line 45, please replace "et al," with -- et al., --.

At column 2, line 45, please delete "," after "is".

At column 8, approximately line 67, please insert "," after "26.2".

At column 11, approximately line 40, please delete "," after "26.1".

At column 12, approximately line 37, after "(d, 1H, J=5 Hz)" please insert -- , --.

At column 18, line 49 in Claim 1, please delete "," after "hydrogen".

At column 18, line 50 in Claim 1, please delete")" after "aryl".

At column 18, line 67 in Claim 1, please replace "or" with -- and --.

At column 19, line 50 in Claim 3, please replace "chloride" with --chlorine --.

At column 19, line 67 in Claim 4, please delete "." after -- group --.

At column 20, approximately line 36 in Claim 4, please move "." next to the last chemical formula down to approximately line 38.

UNITED STATES PATENT AND TRADEMARK OFFICE
CERTIFICATE OF CORRECTION

PATENT NO. : 6,949,654 B2
APPLICATION NO. : 10/456024
DATED : September 27, 2005
INVENTOR(S) : Oh et al.

It is certified that error appears in the above-identified patent and that said Letters Patent is hereby corrected as shown below:

At column 20, approximately line 47 in Claim 7, please insert "," between "claim 6" and "wherein".

At column 20, approximately line 49 in Claim 8, please insert "," between "claim 6" and "wherein".

At column 21, line 11 in Claim 17, please remove the space between "claim" and "1,".

At column 23, line 3 in Claim 19, after "amount", please insert -- of --.

Signed and Sealed this

Eighth Day of August, 2006

JON W. DUDAS
*Director of the United States Patent and Trademark Office*